US012064221B2

(12) United States Patent
Nishida et al.

(10) Patent No.: US 12,064,221 B2
(45) Date of Patent: Aug. 20, 2024

(54) BLOOD PRESSURE MEASUREMENT DEVICE

(71) Applicants: OMRON HEALTHCARE Co., Ltd., Kyoto (JP); OMRON Corporation, Kyoto (JP)

(72) Inventors: Tomoyuki Nishida, Kyoto (JP); Hirokazu Tanaka, Kyoto (JP); Noboru Kohara, Kyoto (JP); Shinji Mizuno, Kyoto (JP)

(73) Assignees: OMRON HEALTHCARE CO. LTD., Kyoto (JP); OMRON CORPORATION, Kyoto (JP)

( * ) Notice: Subject to any disclaimer, the term of this patent is extended or adjusted under 35 U.S.C. 154(b) by 727 days.

(21) Appl. No.: 17/217,188

(22) Filed: Mar. 30, 2021

(65) Prior Publication Data
US 2021/0212579 A1 Jul. 15, 2021

Related U.S. Application Data

(63) Continuation of application No. PCT/JP2019/038333, filed on Sep. 27, 2019.

(30) Foreign Application Priority Data

Oct. 15, 2018 (JP) .................. 2018-194350

(51) Int. Cl.
*A61B 5/021* (2006.01)
*A61B 5/022* (2006.01)

(52) U.S. Cl.
CPC .......... *A61B 5/02141* (2013.01); *A61B 5/022* (2013.01)

(58) Field of Classification Search
CPC ... A61B 5/02; A61B 17/1735; A61B 5/02141; A61B 5/022; A61B 5/6801; A61B 5/683
See application file for complete search history.

(56) References Cited

U.S. PATENT DOCUMENTS 5,032,823 A * 7/1991 Bower .................. G08B 21/22
340/539.31
2006/0184054 A1* 8/2006 Sano ..................... A61B 5/021
600/490

(Continued)

FOREIGN PATENT DOCUMENTS

BR 112015021361 A2 7/2017
CN 105142507 A 12/2015

(Continued)

OTHER PUBLICATIONS

International Preliminary Report on Patentability and Written Opinion of the International Searching Authority issued in Apr. 29, 2021 in International (PCT) Application No. PCT/JP2019/038333.

*Primary Examiner* — Eric F Winakur
*Assistant Examiner* — Abel Seifu Abegaz
(74) *Attorney, Agent, or Firm* — Wenderoth, Lind & Ponack, L.L.P.

(57) ABSTRACT

A blood pressure measurement device includes a curler curving with following a circumferential direction of a portion of a living body where the blood pressure measurement device is attached, a bag-like structure, including two sheet members, and a welded portion, formed by welding edges of the two sheet members, the welded portion, including a plurality of insertion holes, the bag-like structure, being inflated with a fluid and being disposed on an inner circumferential surface of the curler, and a junction means abutting a surface on the living body side of the welded portion and inserted into the plurality of insertion holes to join the welded portion, to the curler.

7 Claims, 30 Drawing Sheets

(56) References Cited

U.S. PATENT DOCUMENTS

| | | | | |
|---|---|---|---|---|
| 2009/0143689 A1* | 6/2009 | Berry | ............... | A63B 69/00 |
| | | | | 482/8 |
| 2016/0029910 A1 | 2/2016 | Taniguchi et al. | | |
| 2016/0038154 A1* | 2/2016 | Cohen | ............... | A61B 17/135 |
| | | | | 606/202 |
| 2019/0290143 A1 | 9/2019 | Iwata et al. | | |

FOREIGN PATENT DOCUMENTS

| | | |
|---|---|---|
| CN | 110198661 A | 9/2019 |
| DE | 112014001127 T5 | 11/2015 |
| DE | 112017006627 T5 | 9/2019 |
| JP | 2014-171606 A | 9/2014 |
| JP | 2015-100406 A | 6/2015 |
| JP | 2018-102743 A | 7/2018 |
| JP | 2018-102859 A | 7/2018 |
| WO | 2014/136818 A1 | 9/2014 |

\* cited by examiner

[FIG. 1]
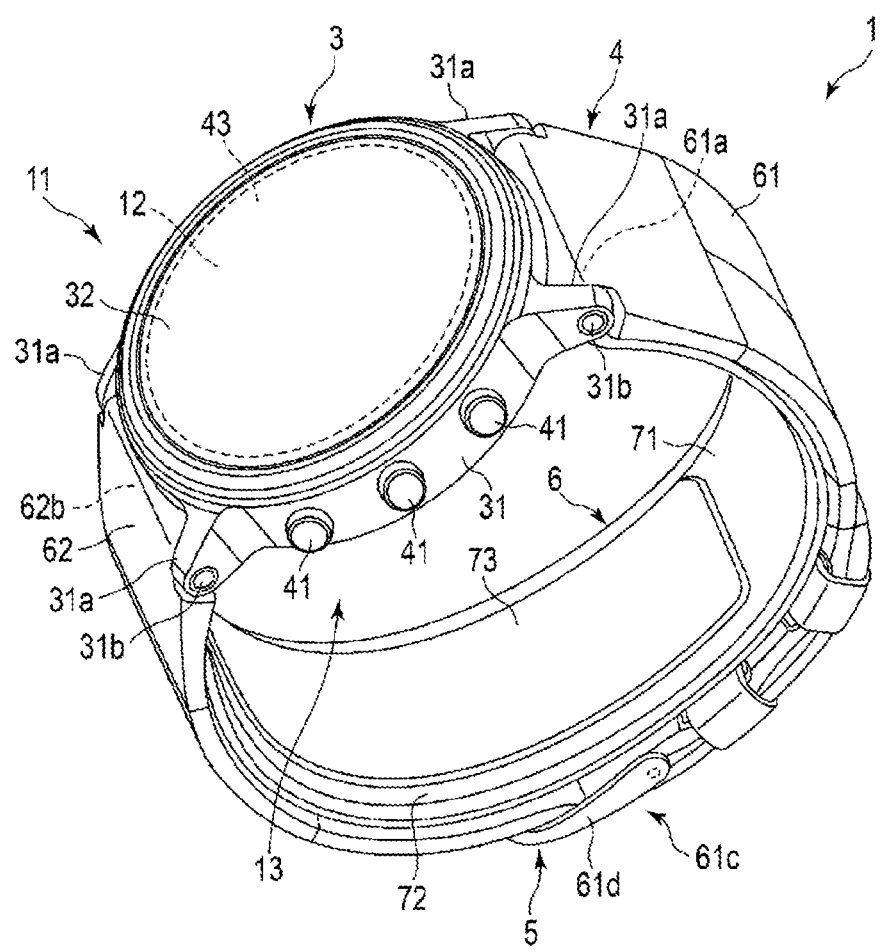

[FIG. 2]
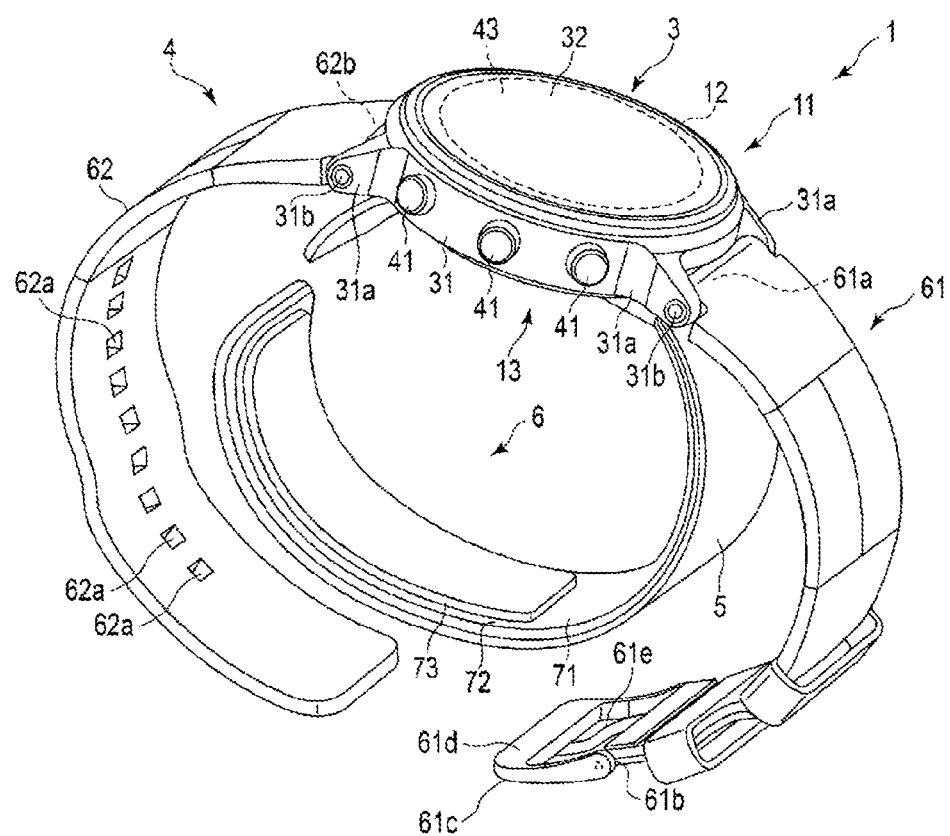

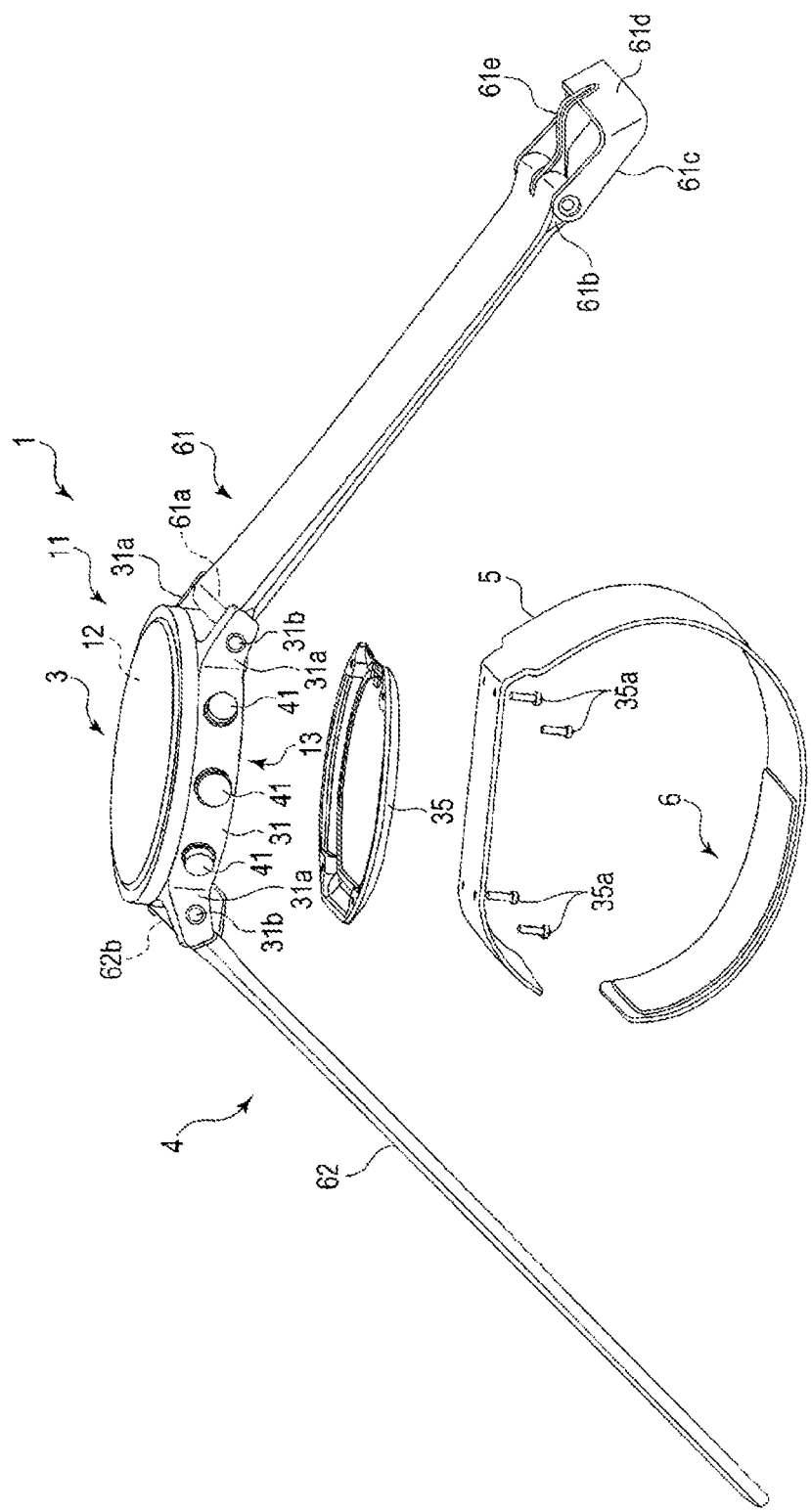
[FIG. 3]

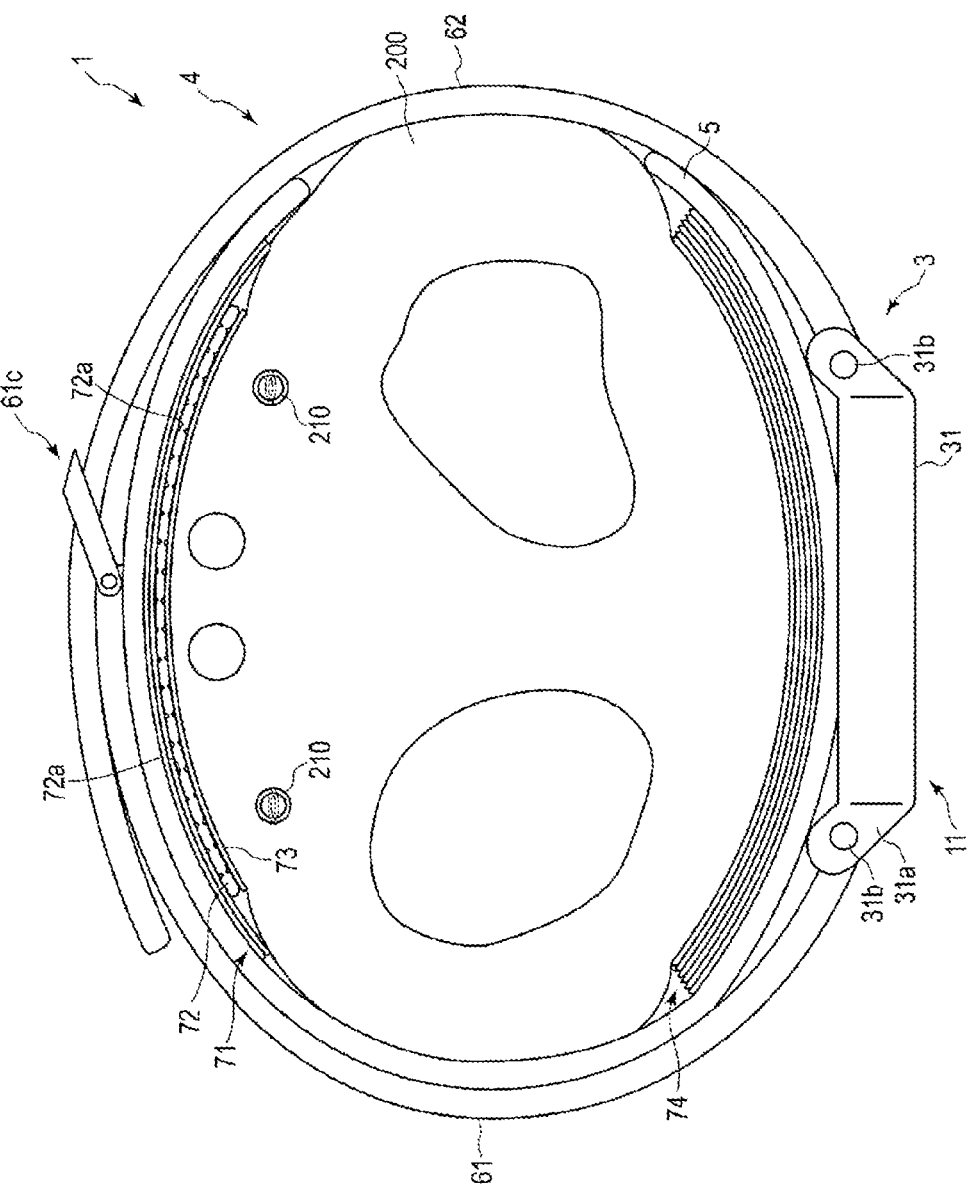
[FIG. 4]

[FIG. 5]
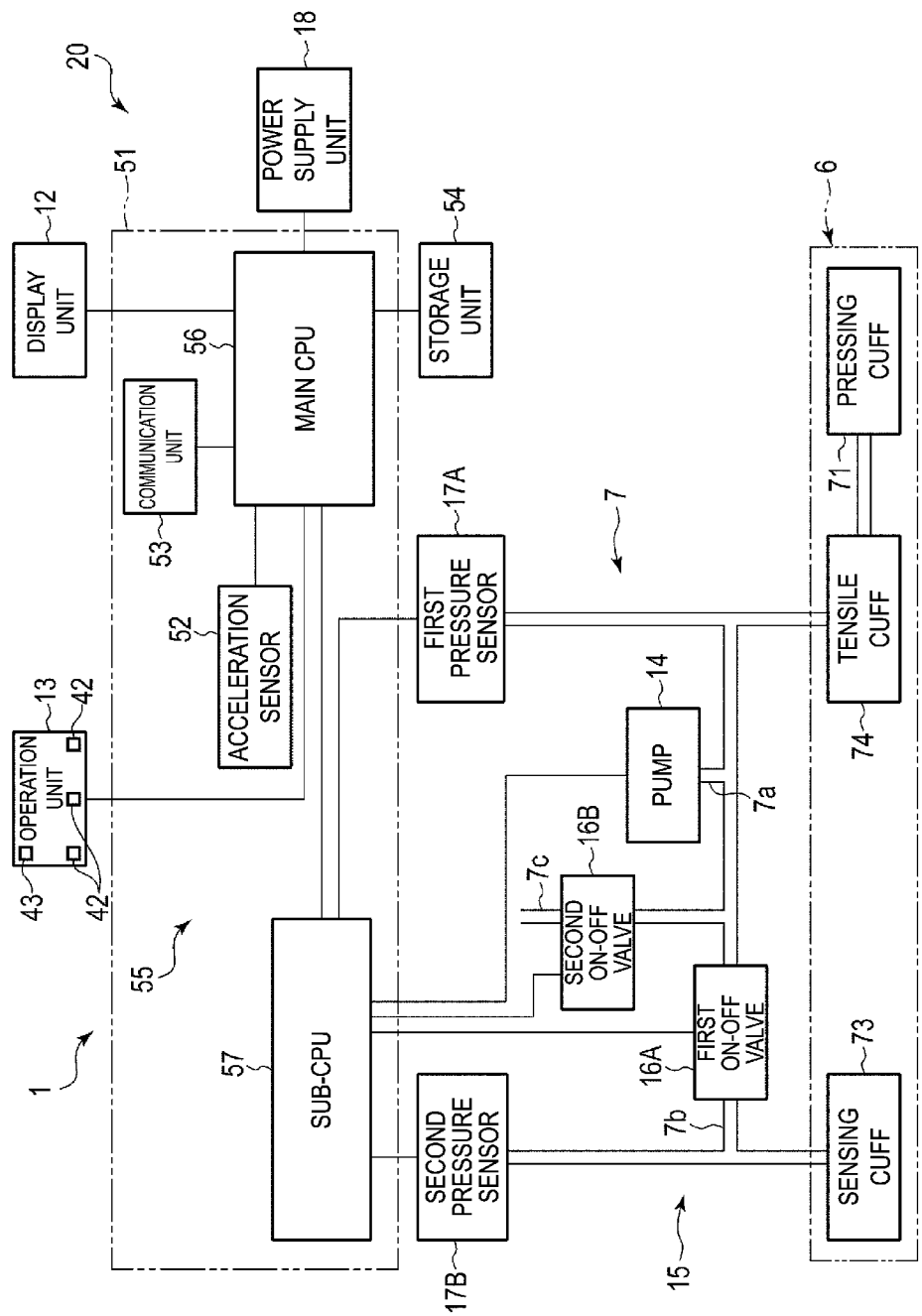

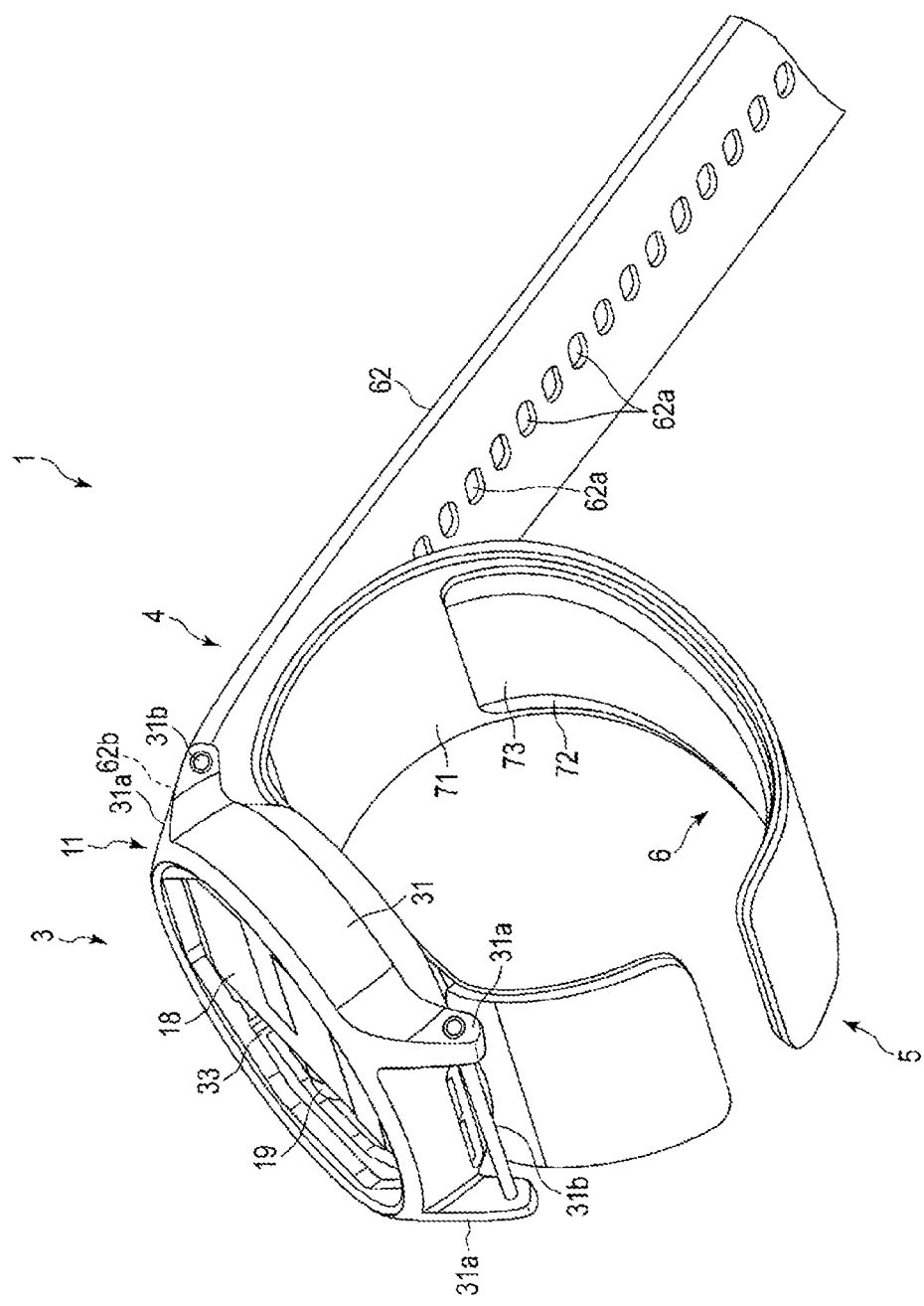
[FIG. 6]

[FIG. 7]
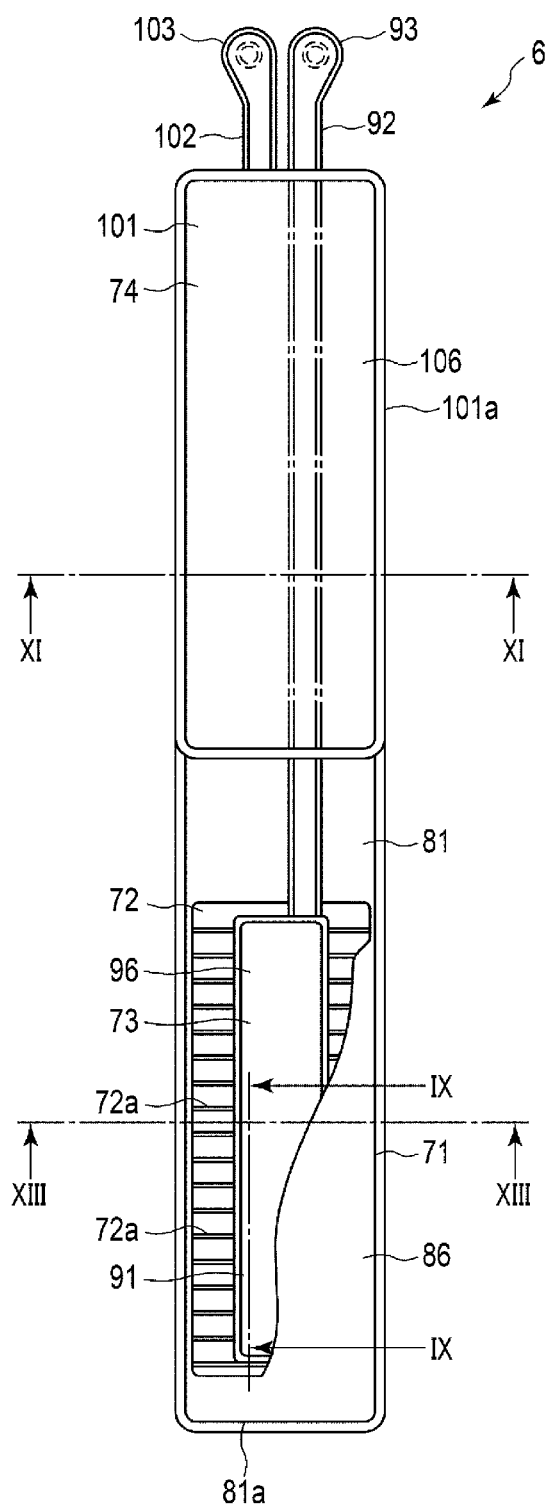

[FIG. 8]
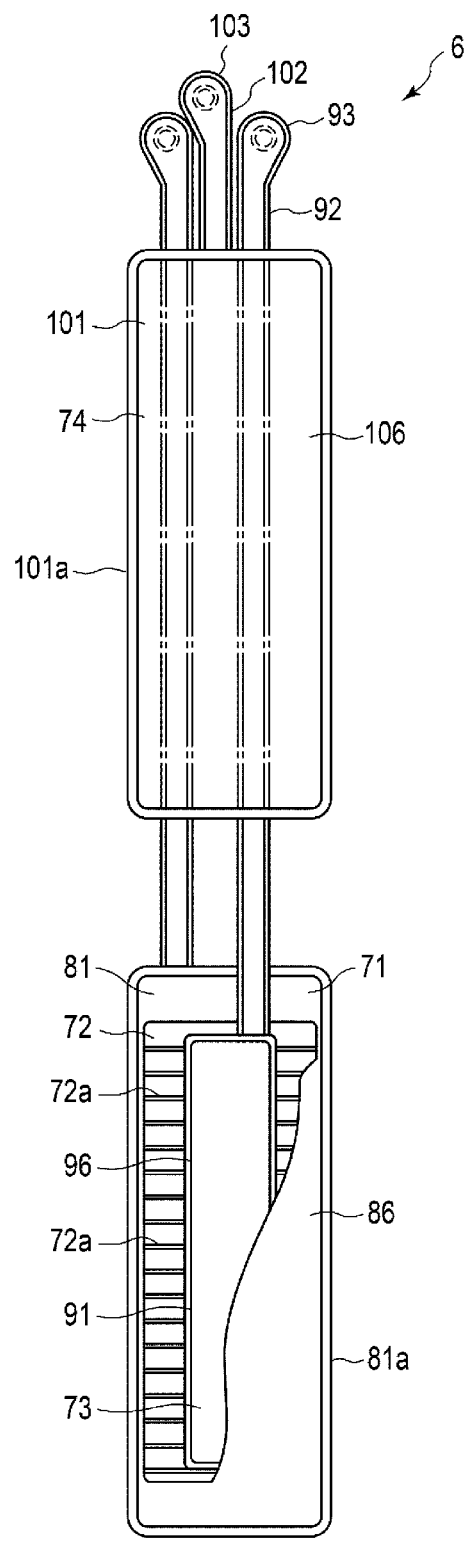

[FIG. 9]
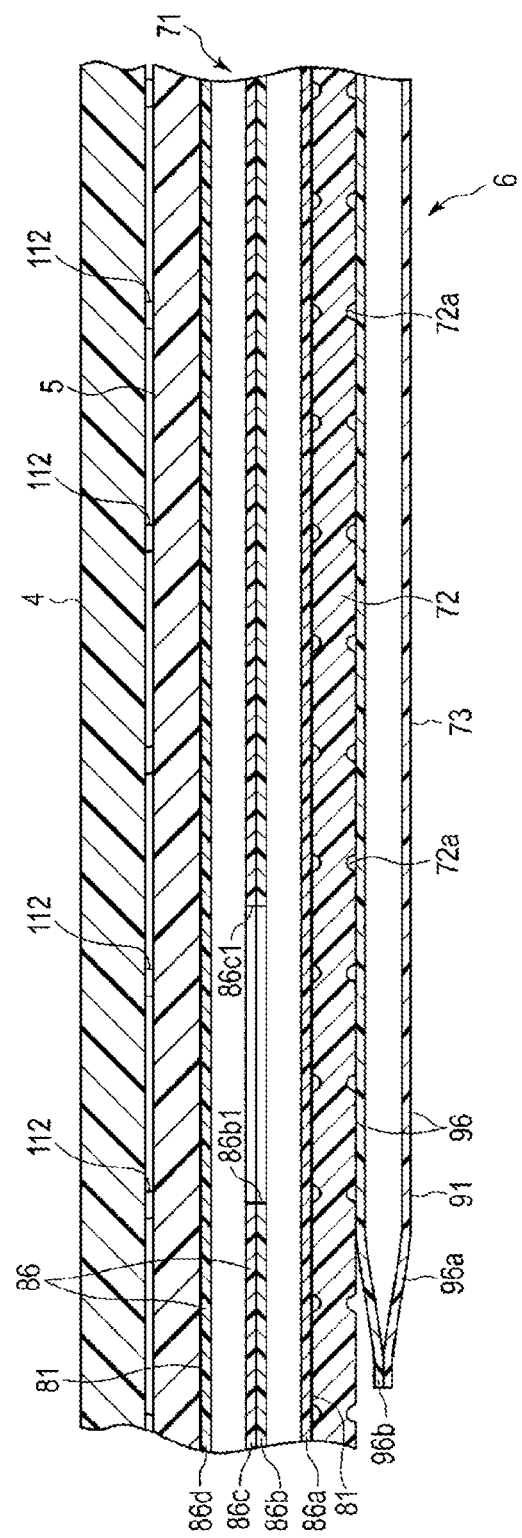

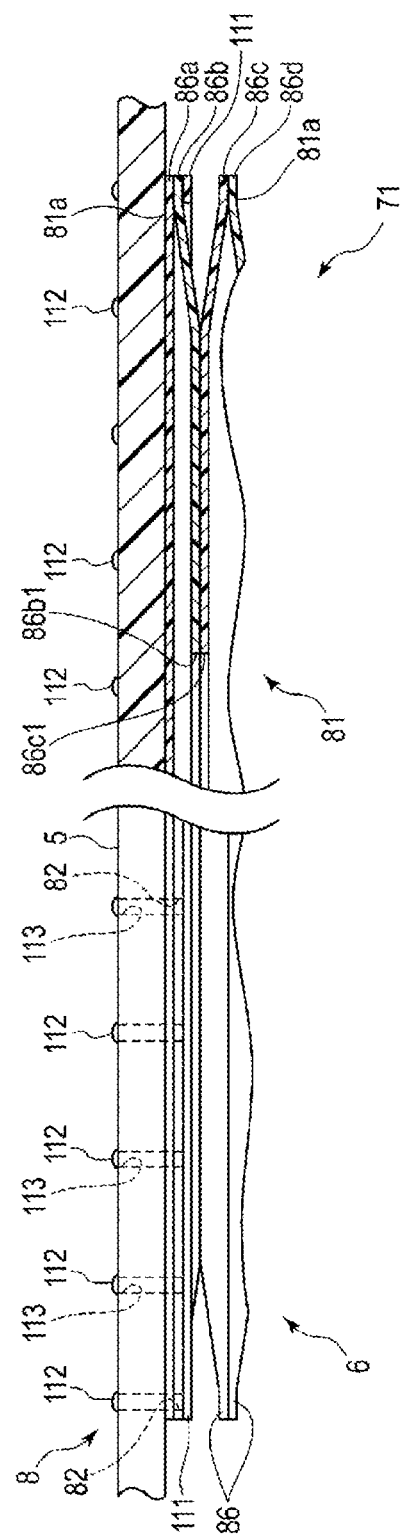

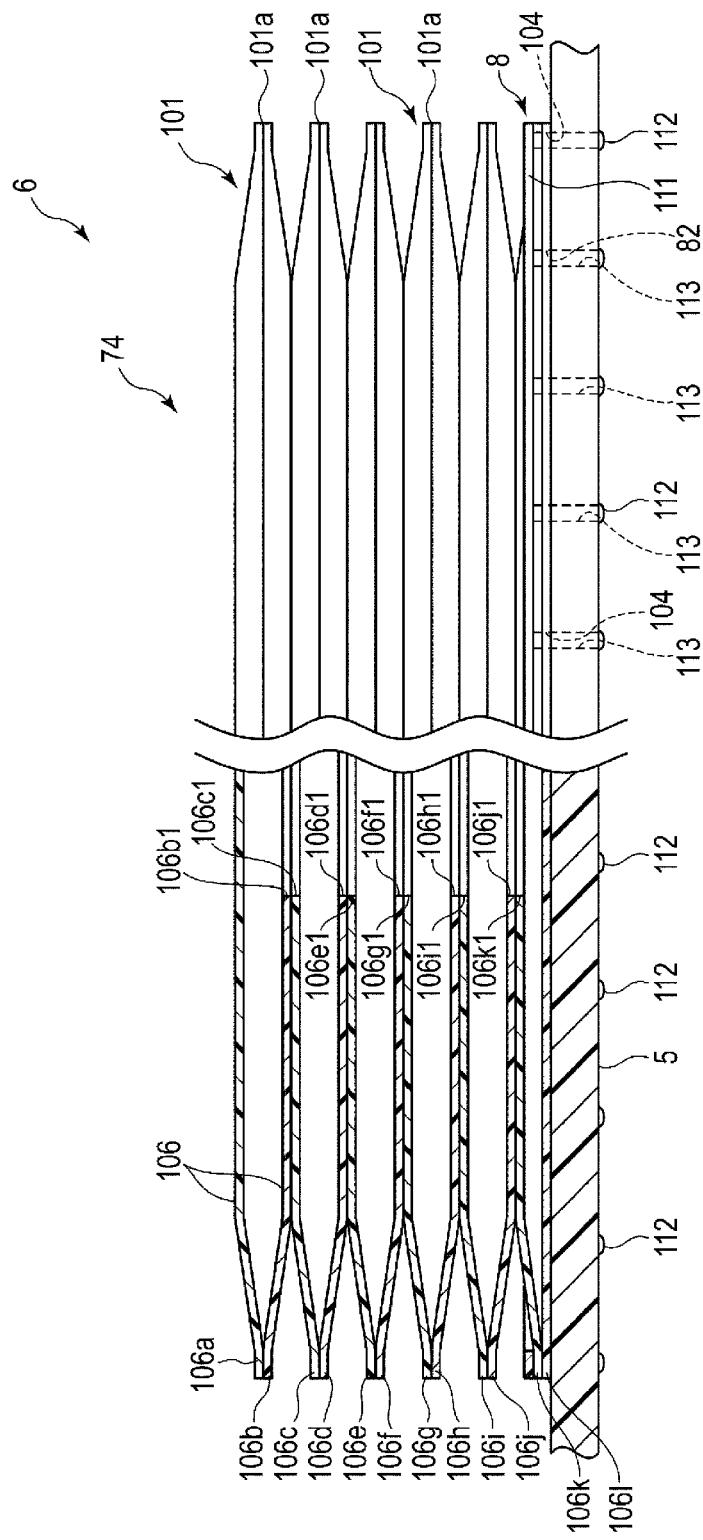

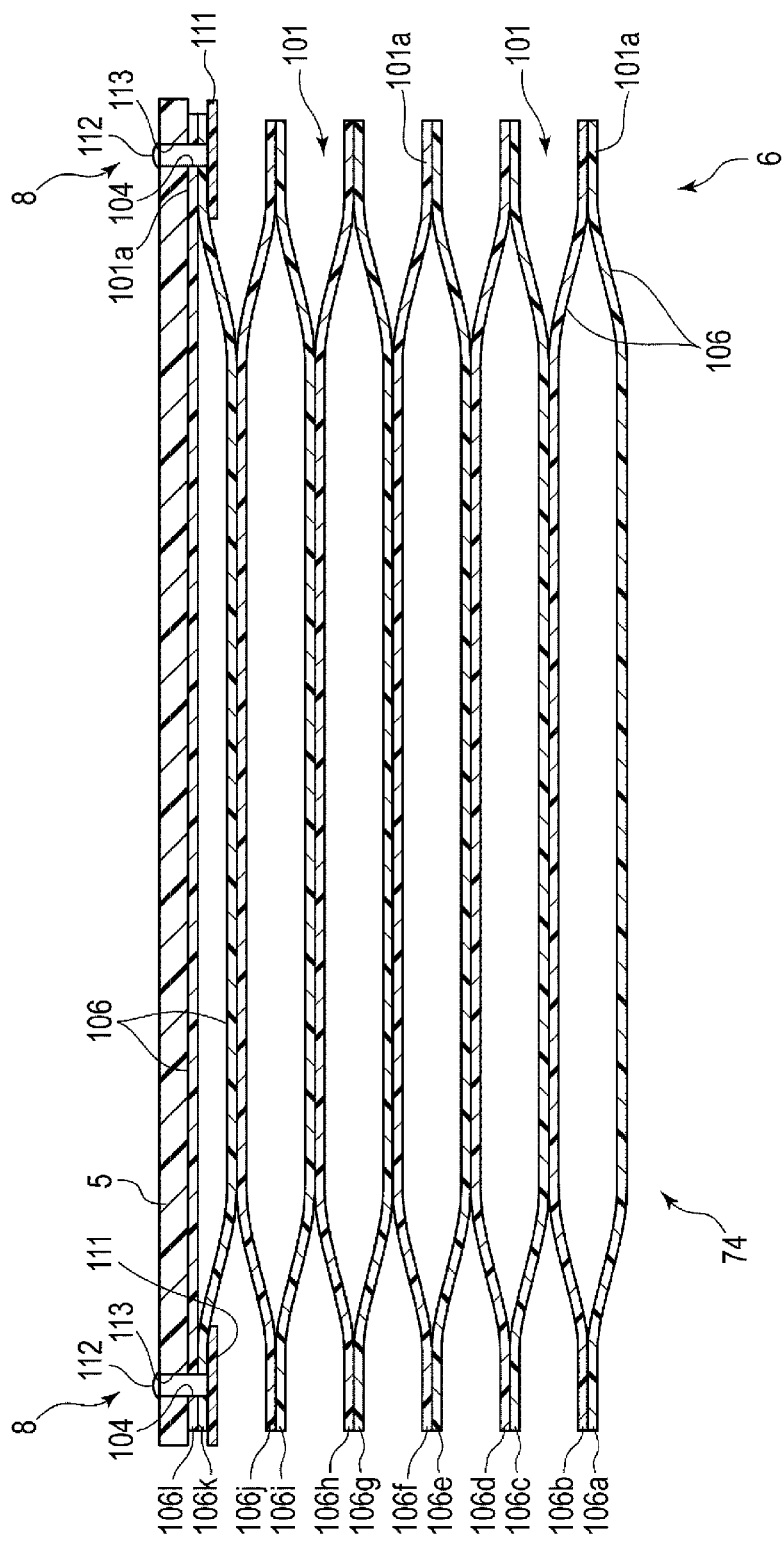

[FIG. 13]
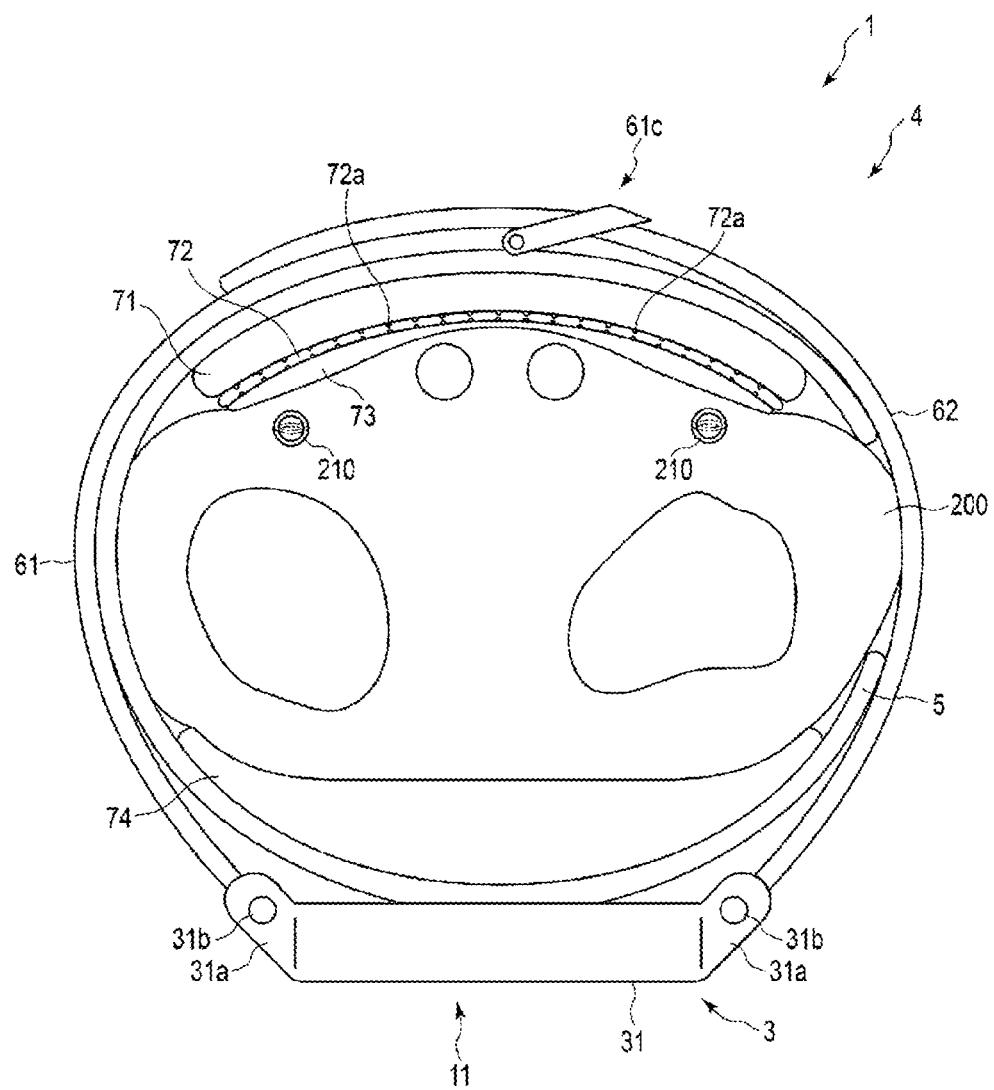

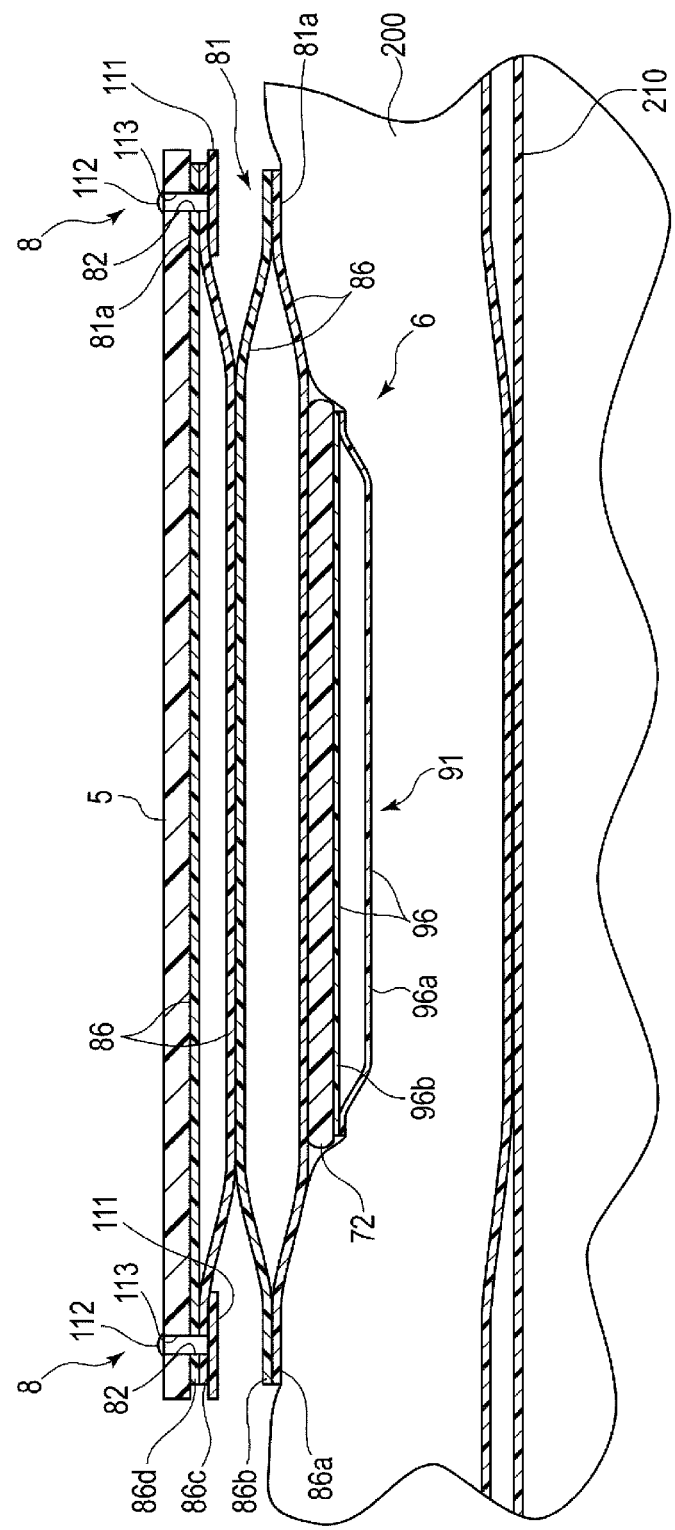
[FIG. 14]

[FIG. 15]
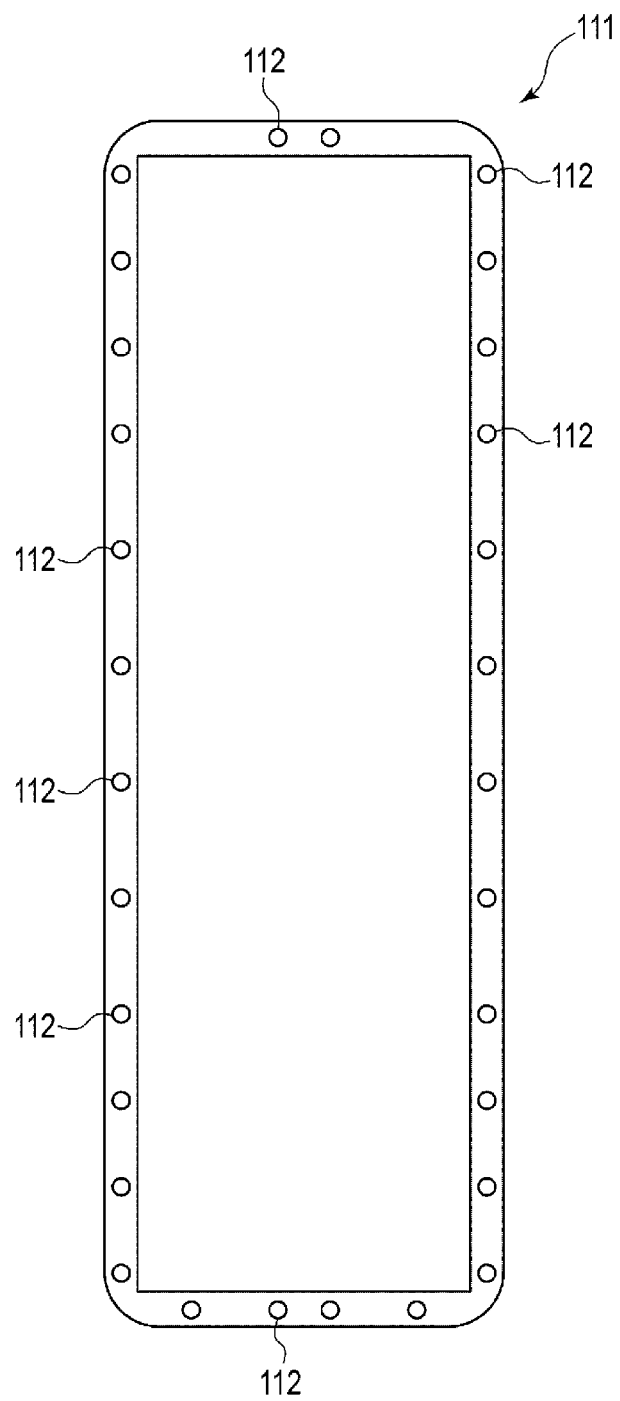

[FIG. 16]
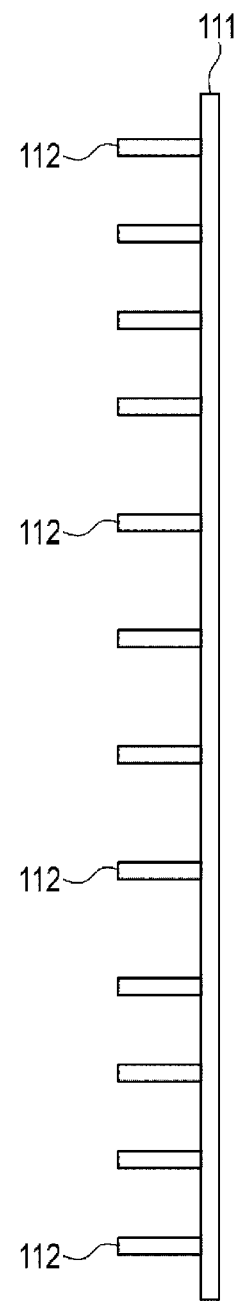

[FIG. 17]
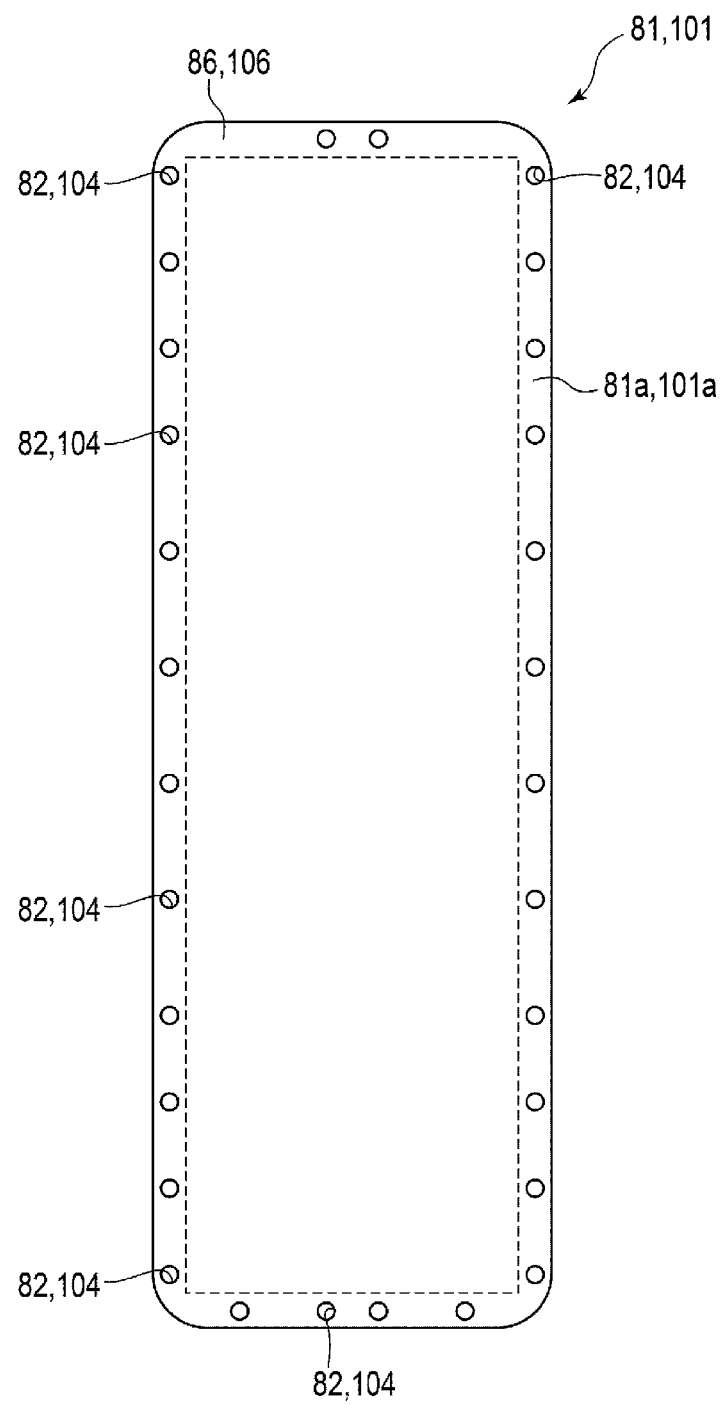

[FIG. 18]
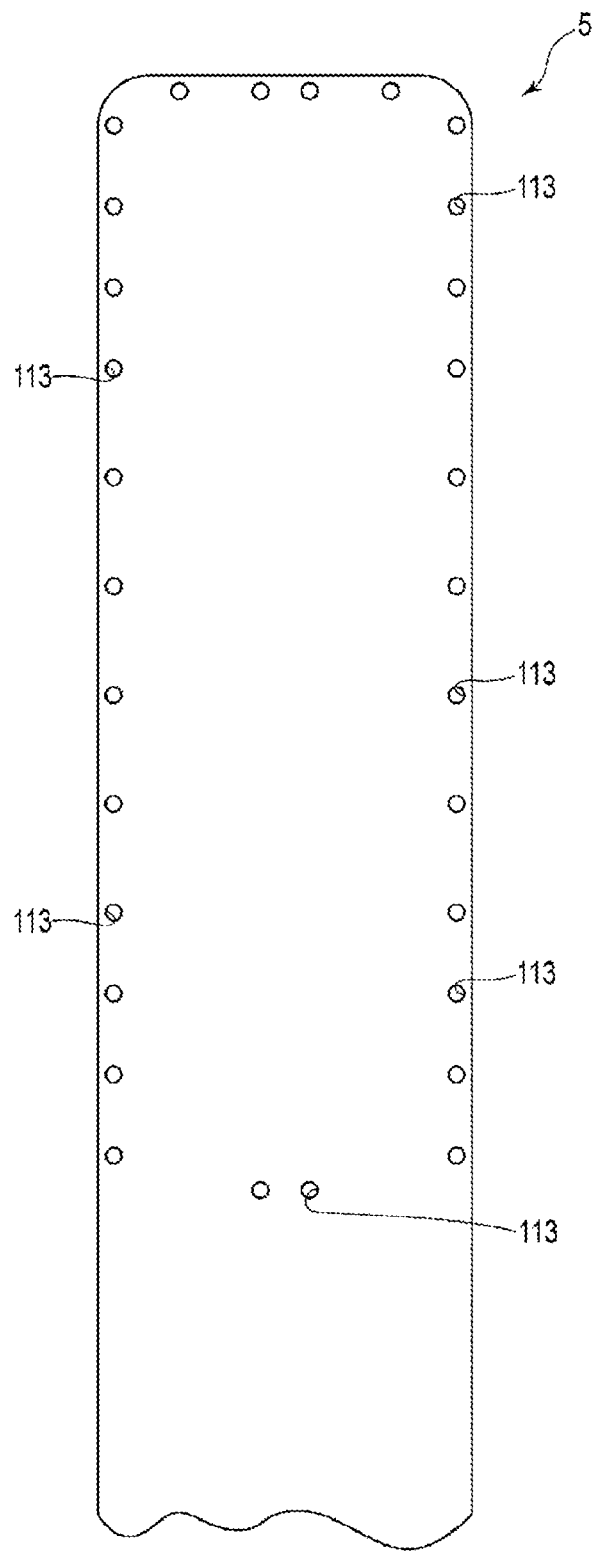

[FIG. 19]
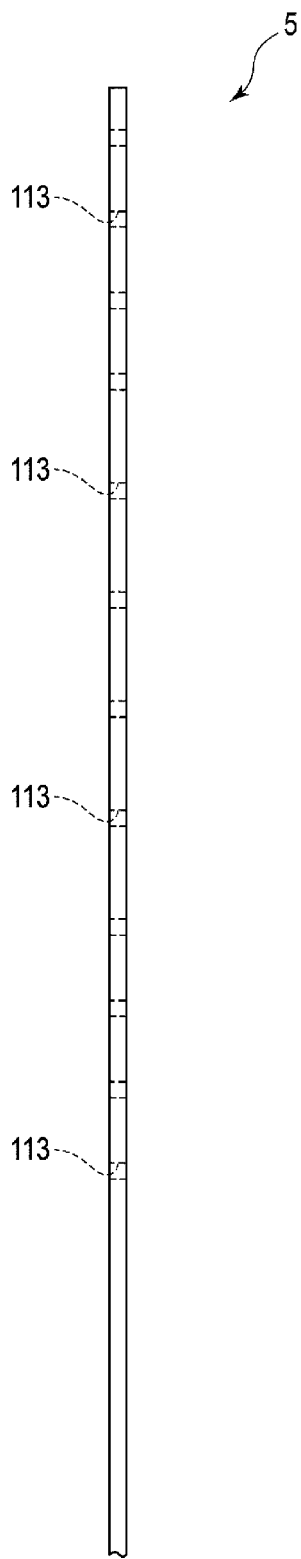

[FIG. 20]
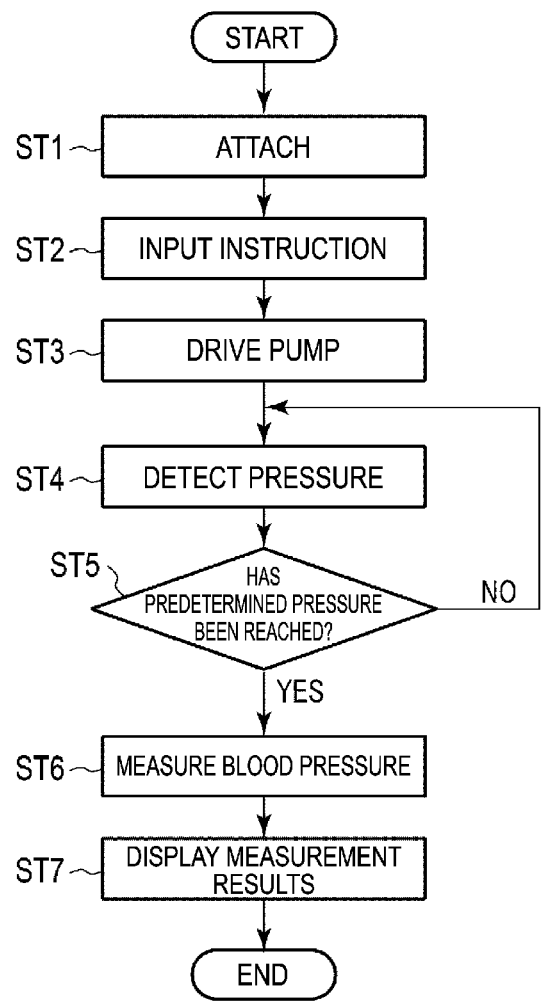

[FIG. 21]
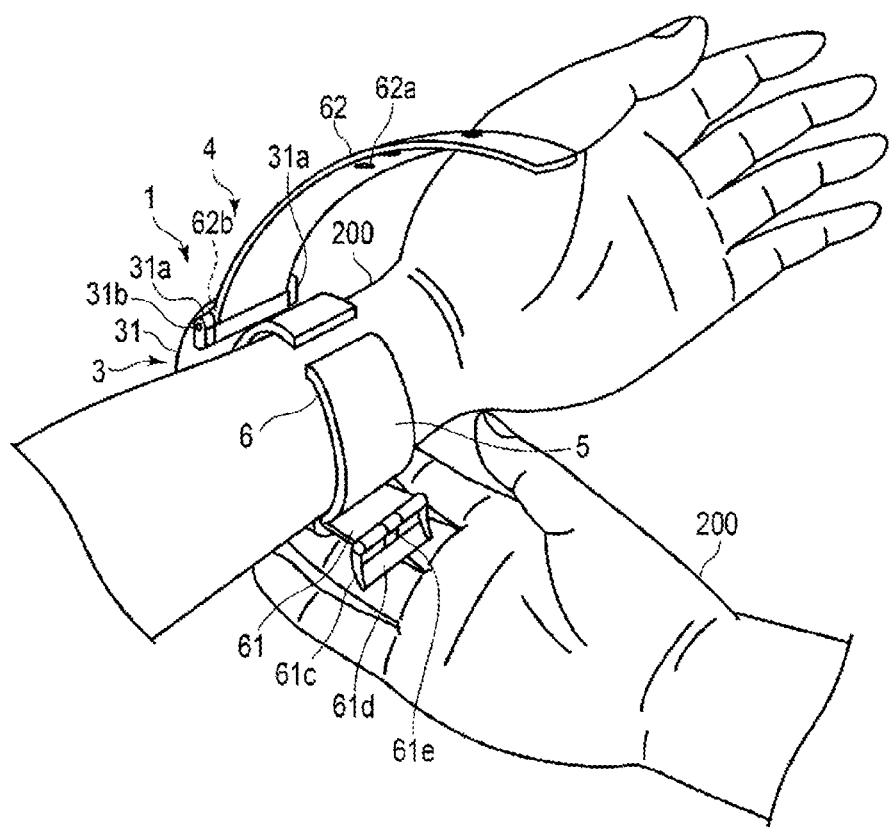

[FIG. 22]
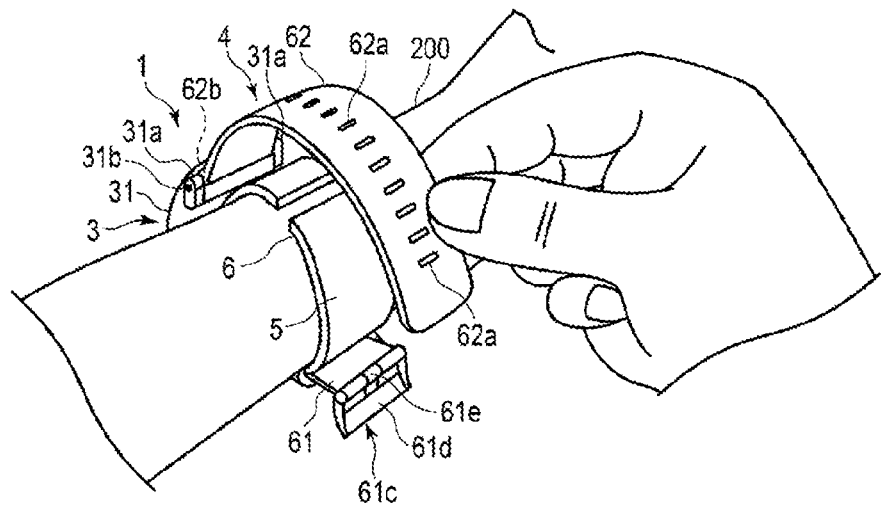
[FIG. 23]
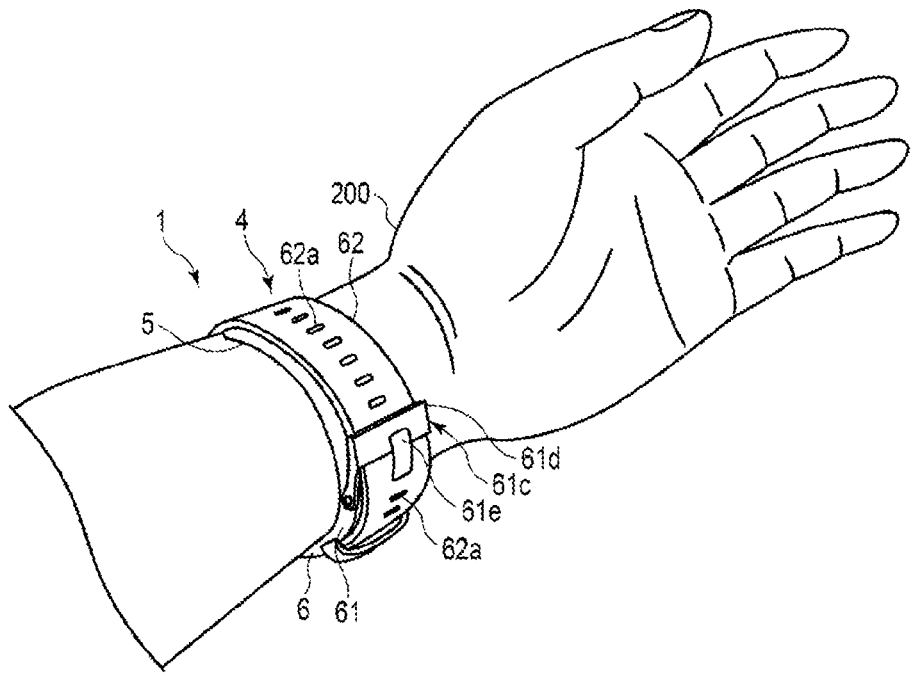

[FIG. 24]
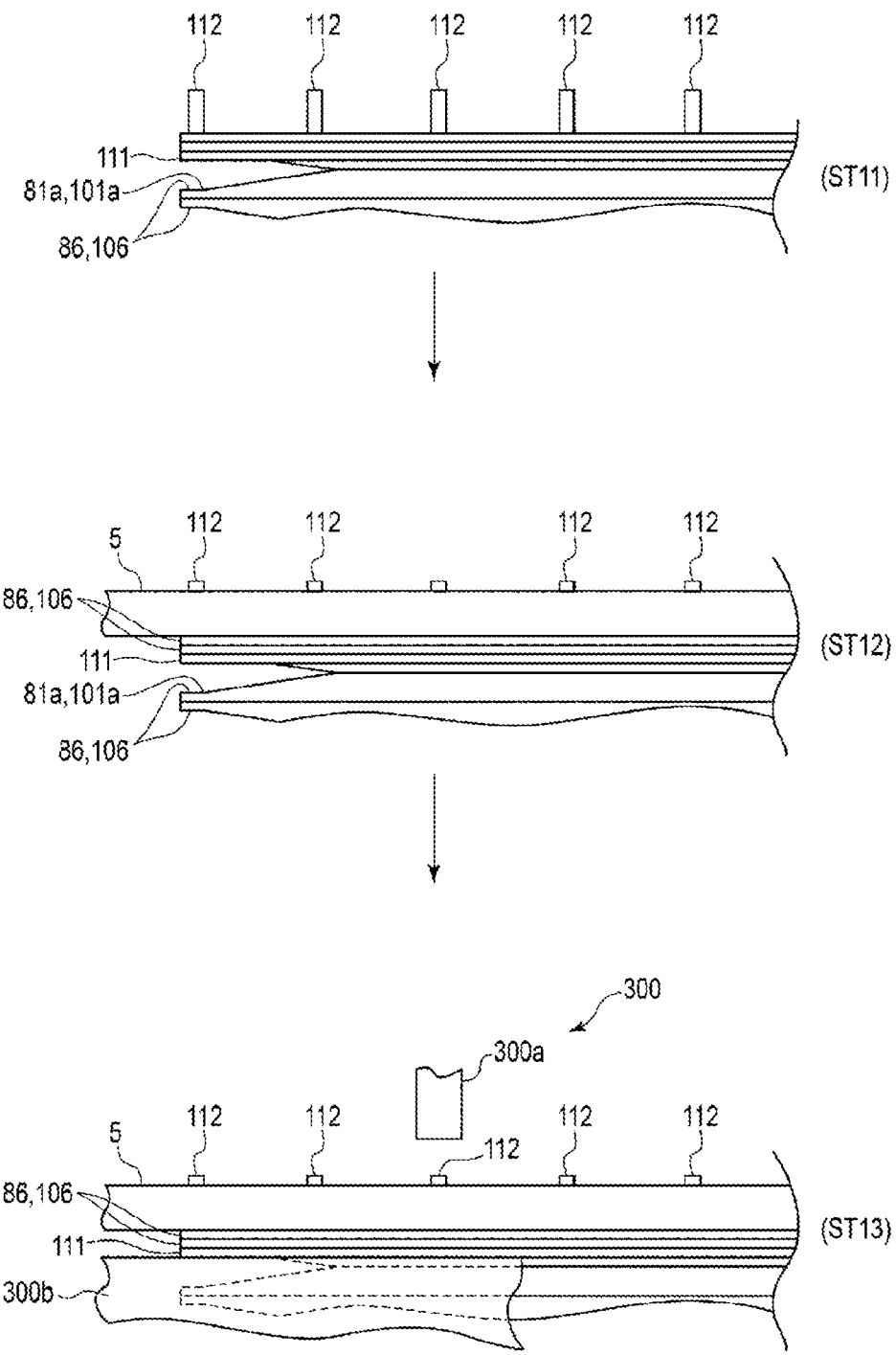

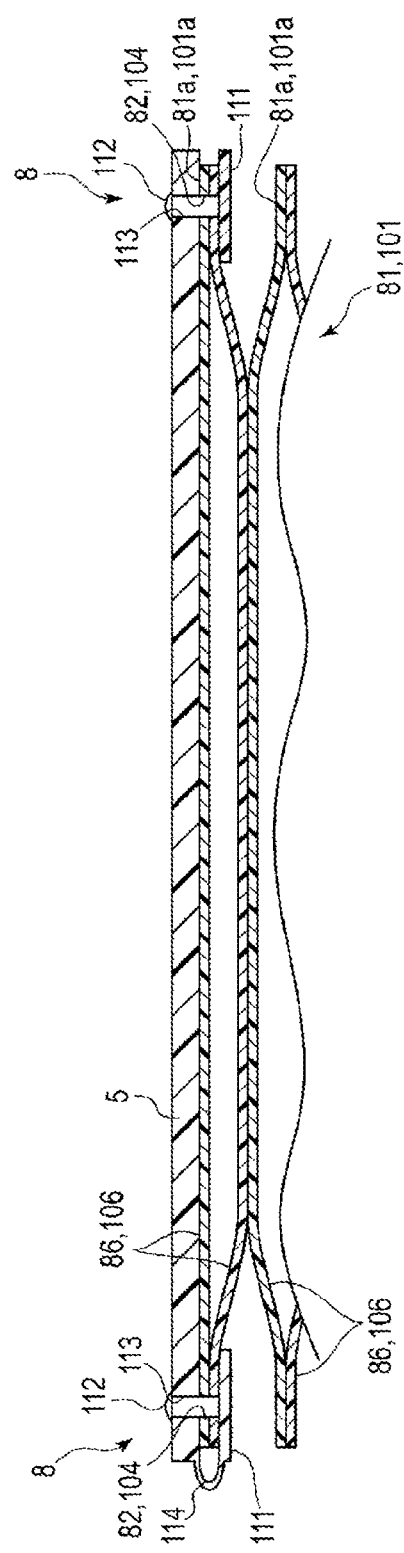

[FIG. 26]
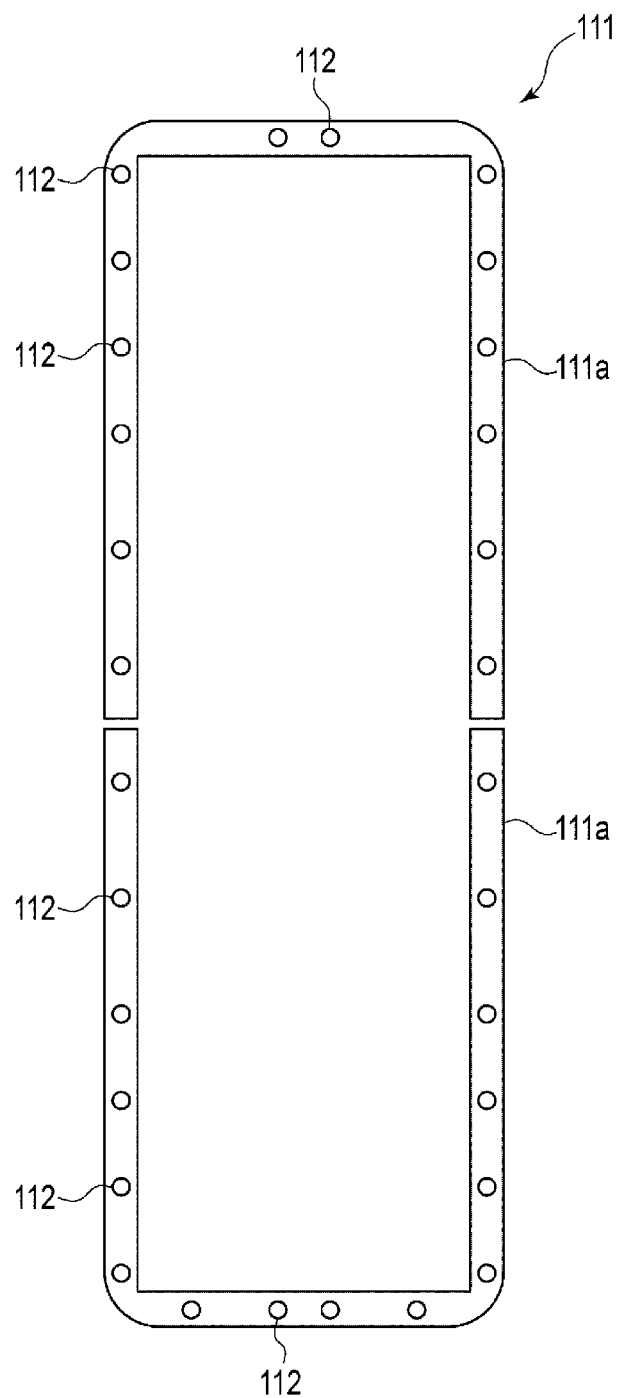

[FIG. 27]
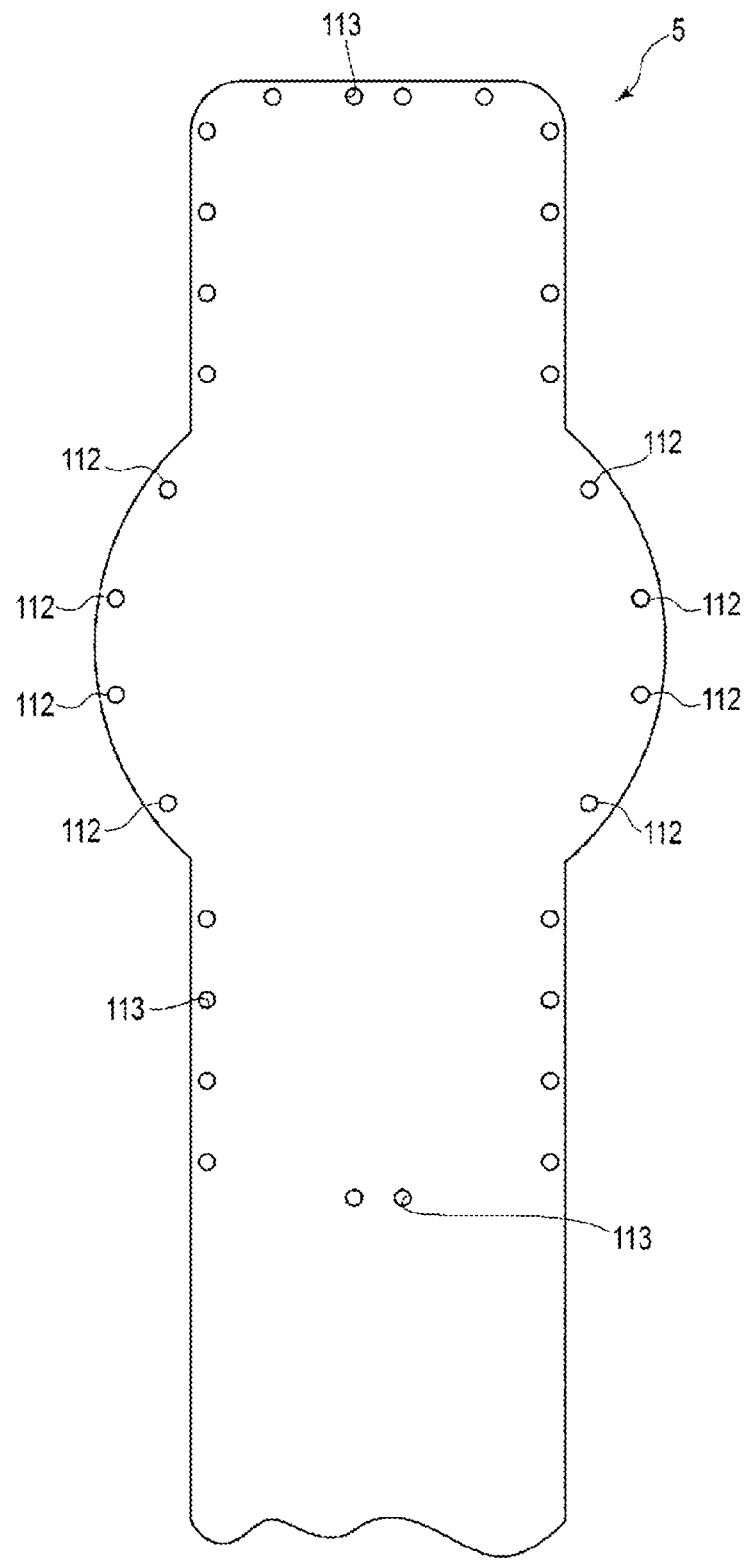

[FIG. 28]
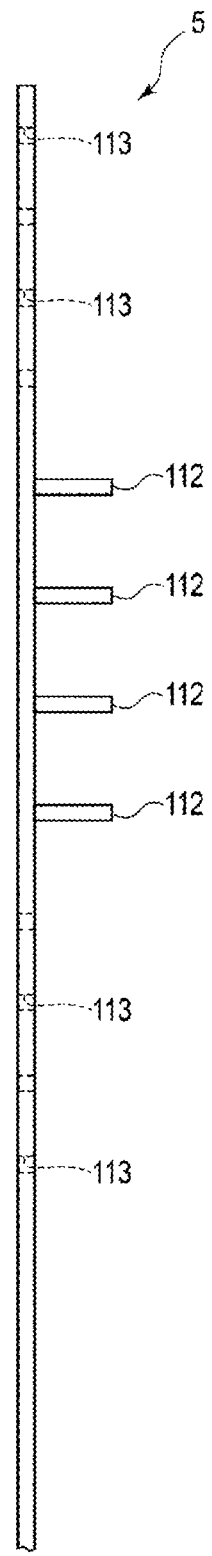

[FIG. 29]
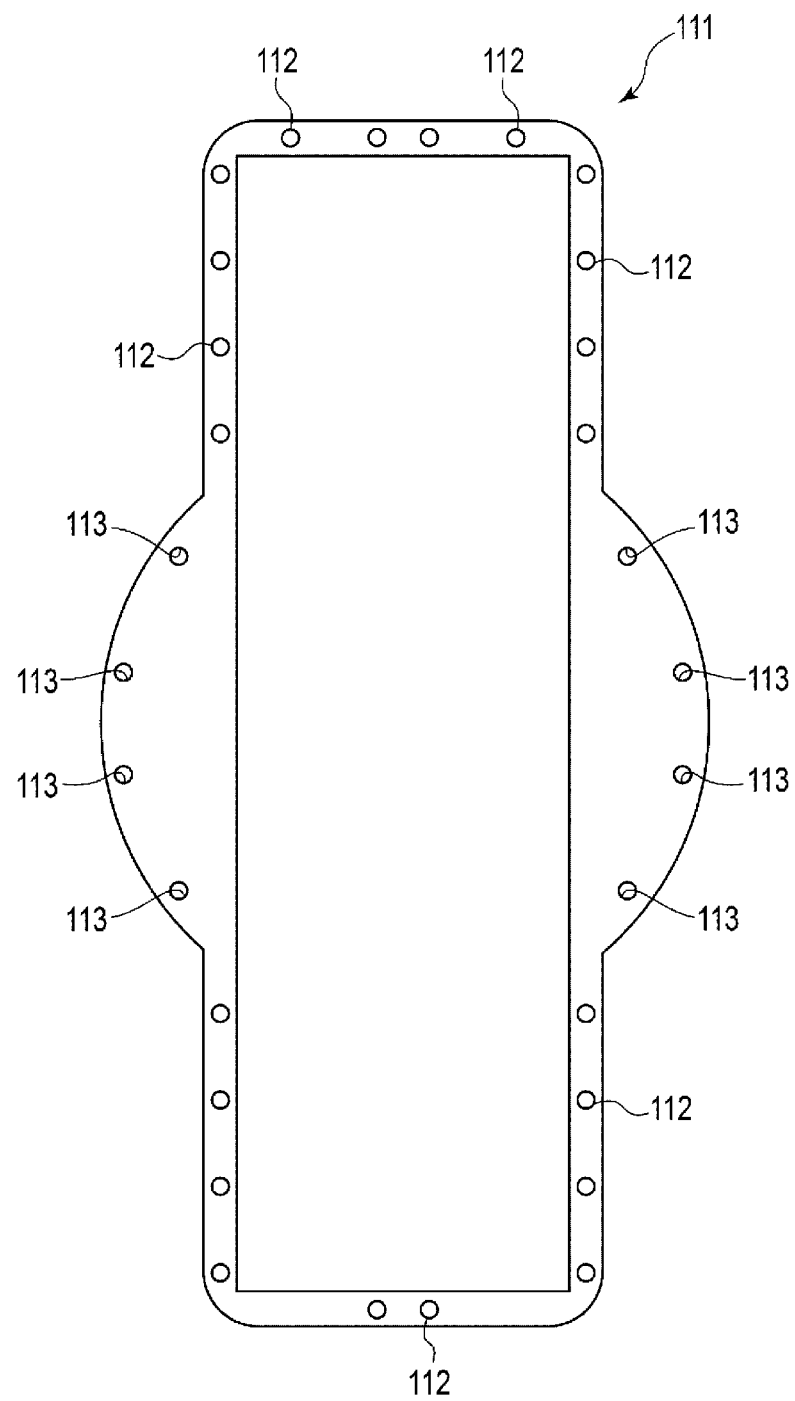

[FIG. 30]
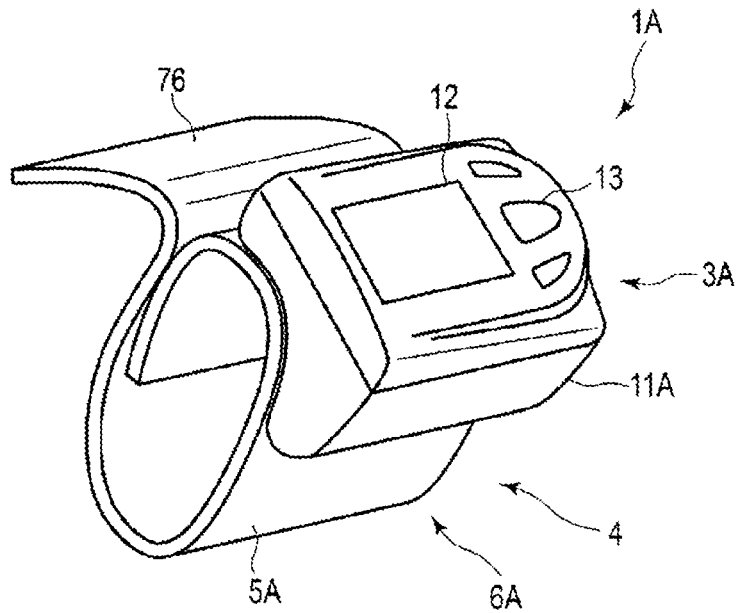
[FIG. 31]
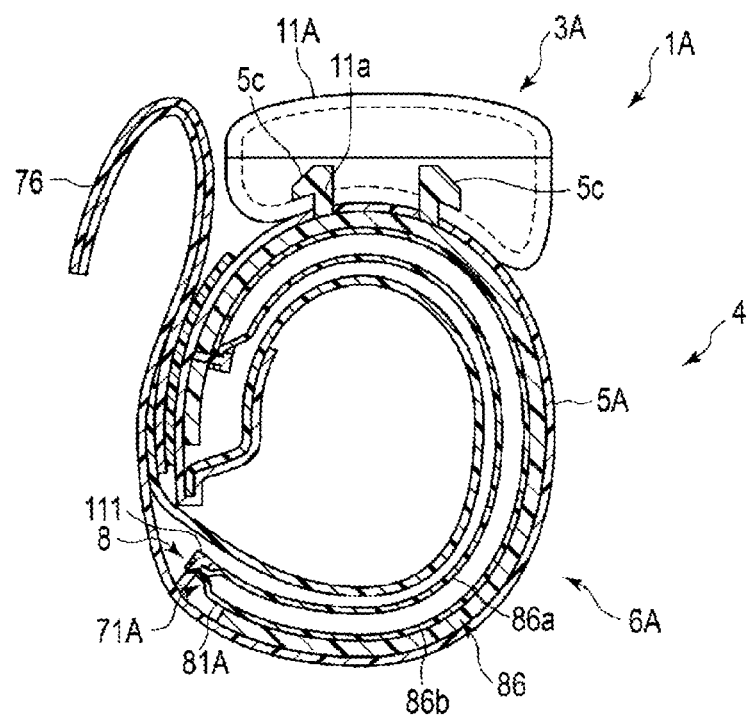

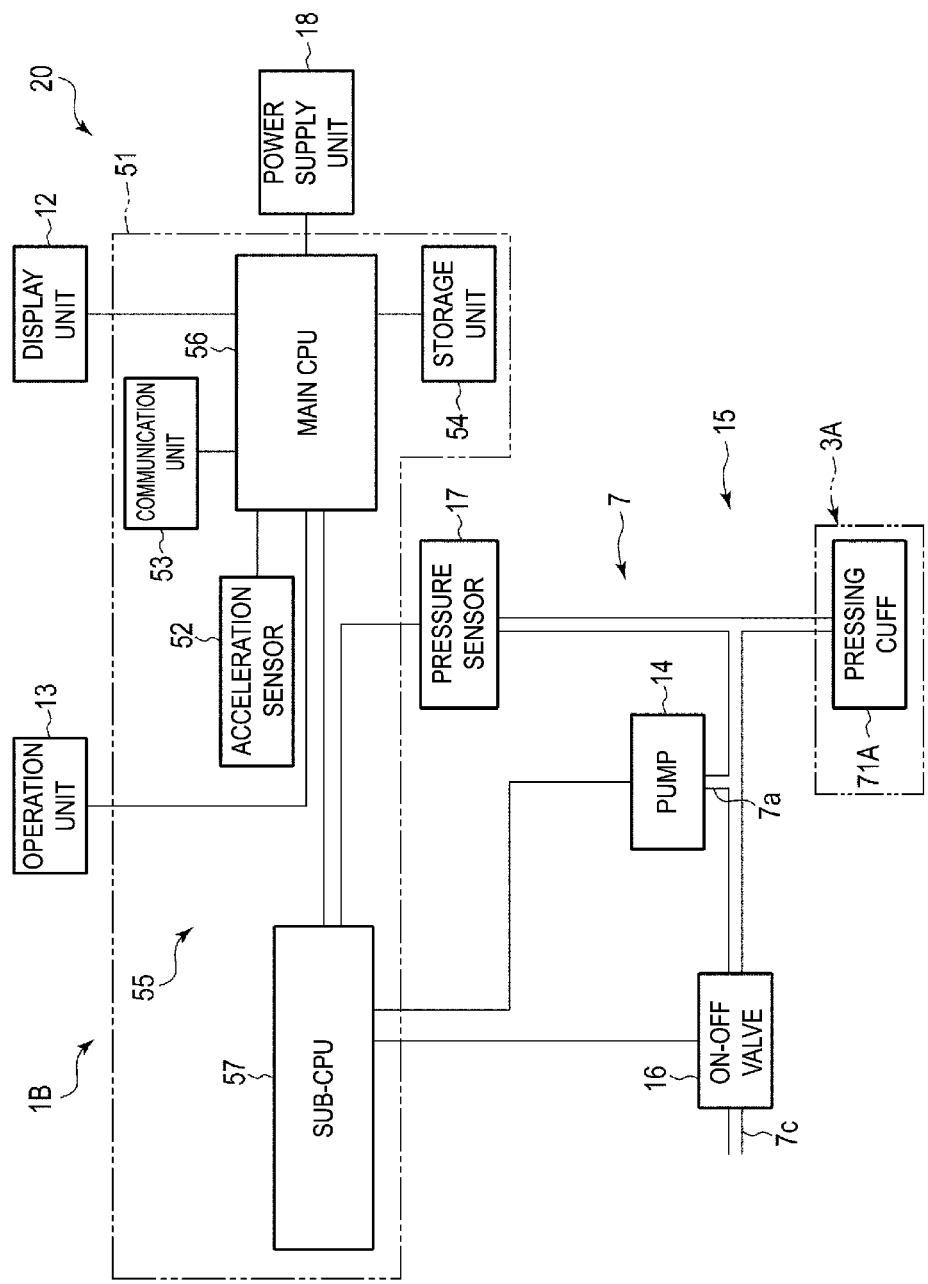
[FIG. 32]

BLOOD PRESSURE MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/038333, filed Sep. 27, 2019, which application claims priority from Japanese Patent Application No. 2018-194350, filed Oct. 15, 2018, which applications are incorporated herein by reference in their entireties.

TECHNICAL FIELD

The present invention relates to a blood pressure measurement device for measuring blood pressure.

BACKGROUND ART

In recent years, blood pressure measurement devices for measuring blood pressure are being used to monitor health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor.

As such a blood pressure measurement device, for example, a so-called integral type is known in which a cuff is integrated with a device body feeding a fluid to the cuff. Such blood pressure measurement devices pose a problem in that wrinkles, folds, or the like in the cuff reduce the accuracy of measurement results for the measured blood pressure. Additionally, in the blood pressure measurement device, the cuff needs to be inflated in the direction in which the blood vessels are occluded and to closely contact the wrist.

Thus, a technique for a blood pressure measurement device is known in which a curler is used between a belt and the cuff to bring the cuff inflated into close contact with the upper arm or the wrist as disclosed in JP 2018-102743 A. In such a blood pressure measurement device, the curler is integrally constituted with the cuff by bonding and fixing the curler to the cuff with a bonding layer, such as double-sided tape.

CITATION LIST

Patent Literature

Patent Document 1: JP 2018-102743 A

SUMMARY OF INVENTION

Technical Problem

In the blood pressure measurement device described above, when the cuff is inflated, a central side of the cuff bulges more significantly than an edge side of the cuff. When the central side of the cuff bulges more significantly than the end portion side of the cuff, stress applied to the bonding layer bonding the cuff to the curler is concentrated on the edge side of the cuff. Thus, stress occurs in the bonding layer such that the cuff peels off from the curler originating from the edge side of the cuff. Thus, repeated inflation and contraction of the cuff may cause the cuff to be peeled off from the curler. In particular, reduced widths of the curler and the cuff reduce the area in which the cuff and the curler are bonded, making the cuff more easily peeled off from the curler. Thus, the joining strength between the curler and the cuff may be enhanced by increasing the widths of the cuff and the curler.

However, a wearable device attached to the wrist has been proposed for a blood pressure measurement device, and there has been a demand for further miniaturization. Thus, there has been a demand for a technique that can enhance the joining strength between the cuff and the curler without increasing the widths of the cuff and the curler.

Thus, an object of the present invention is to provide a blood pressure measurement device that can enhance the joining strength between the cuff and the curler.

Solution to Problem

According to one aspect, a blood pressure measurement device is provided that includes a curler curving with following a circumferential direction of a portion of a living body where the blood pressure measurement device is attached, a bag-like structure including two sheet members and a welded portion formed by welding edges of the two sheet members, and the welded portion including a plurality of insertion holes, the bag-like structure being inflated with a fluid and being disposed on an inner circumferential surface of the curler, and a junction means abutting a surface on the living body side of the welded portion and inserted into the plurality of insertion holes to join the welded portion to the curler.

Here, the fluid includes a liquid and air. The bag-like structure constitutes the cuff by being wrapped around the upper arm, the wrist, or the like of a living body and inflated by being fed with the fluid, when the blood pressure is measured. The junction means refer to members that mechanically join the two members, and include, for example, protrusions for swaging, rivets, stitching threads, and the like.

According to this aspect, since the bag-like structure can be mechanically joined to the curler, the bag-like structure can be firmly joined to the curler. Thus, the blood pressure measurement device can enhance the joining strength between the cuff and the curler. In addition, the bag-like structure is formed by welding two sheet members, and when the welded portion formed by welding the two sheet members are provided with the insertion holes through which the junction means are inserted, the welded portion can be used as a junction margin. This configuration eliminates a need for separate junction margins for joining the bag-like structure to the curler, enabling the blood pressure measurement device to be miniaturized.

In the blood pressure measurement device of the one aspect described above, a blood pressure measurement device is provided, in which the junction means includes a substrate having a frame-shape and being disposed facing the welded portion, a plurality of protrusions integrally formed on at least one of the curler or the substrate and inserted into the plurality of insertion holes, and a plurality of junction target holes formed in at least one of the substrate or the curler, the plurality of protrusions being inserted and joined to the plurality of junction target holes.

According to this aspect, the curler and the substrate are provided with the plurality of protrusions inserted into the insertion holes and the plurality of junction target holes to which the plurality of protrusions are joined. For this reason, by disposing the bag-like structure between the curler and the substrate and joining the curler and the substrate with the protrusions and the junction target holes, the bag-like structure can be mechanically joined to the curler. In addition, the substrate has a frame shape disposed facing the welded portion, and thus inflation of the bag-like structure is prevented from being inhibited.

In the blood pressure measurement device of the one aspect described above, a blood pressure measurement device is provided, in which the plurality of protrusions are formed of a thermoplastic resin material and are thermally swaged.

According to this aspect, the plurality of protrusions can be thermally swaged, and the protrusions are thus easily swaged.

In the blood pressure measurement device of the one aspect described above, a blood pressure measurement device is provided, in which the curler and the substrate are formed of a thermoplastic resin.

According to this aspect, because the curler and the substrate are formed of the thermoplastic resin material, when the plurality of protrusions are thermally swaged, the curler or the substrate provided with the plurality of junction target holes are also heated together. Thus, in addition to the junction with swaging of the protrusions, welding of the curler or the substrate provided with protrusions and junction target holes can be achieved. Thus, the joining strength between the substrate and the curler is enhanced, and as a result, the joining strength between the curler and the bag-like structure disposed between the substrate and the curler is enhanced.

In the blood pressure measurement device of the one aspect described above, a blood pressure measurement device is provided, in which the plurality of protrusions, the curler, and the substrate are formed of similar materials, and the plurality of protrusions are thermally welded to the curler or the substrate.

In this regard, "similar materials" refer to two materials that are highly compatible with each other in thermal welding and that have the same softening temperature or close softening temperatures. "Compatibility" refers to the degree of mixing of the resin materials softened or melted during welding, and "high compatibility" means that junction can be achieved in which the resin materials softened or melted during welding mix together at a suitable degree, that is, junction can be achieved at a required junction strength.

According to this aspect, when the protrusions, the curler, and the substrate include similar materials, the curler or the substrate provided with the protrusions and the junction target holes can be suitably joined by thermal welding, and the curler and the substrate can thus be firmly joined. As a result, the joining strength between the curler and the bag-like structure disposed between the substrate and the curler is enhanced.

In the blood pressure measurement device of the one aspect described above, a blood pressure measurement device is provided, in which the curler and the substrate are integrally molded, and include a hinge portion with which the curler and the substrate are connected.

According to this aspect, the configuration, in which the curler and the substrate are integrally connected with the hinge portion in between, enables the curler and the substrate to be integrally molded by molding. This allows easy manufacturing, and a reduction in the number of components. Furthermore, rotating the curler and the substrate around the hinge portion allows the curler and the substrate to face each other, eliminating a need for alignment between the plurality of protrusions and the plurality of junction target holes. This allows the curler and the substrate to be easily assembled.

In the blood pressure measurement device of the one aspect described above, a blood pressure measurement device is provided, in which the bag-like structure is constituted being long in one direction, and the substrate is divided into a plurality of portions in a longitudinal direction.

According to this aspect, the configuration, in which the frame shaped substrate is divided into the portions, allows the substrate to be easily disposed at the welded portion of the bag-like structure, for example, even in a case where a plurality of bag-like structures are stacked.

In the blood pressure measurement device of the one aspect described above, a blood pressure measurement device is provided, in which a plurality of the bag-like structures are stacked, the plurality of insertion holes are provided in the welded portion of the bag-like structure facing the curler, the plurality of protrusions are provided on the substrate, and the plurality of junction target holes are provided in the curler.

According to this aspect, in a case where a plurality of the bag-like structures are provided, the protrusions are swaged on an outer surface side of the curler. Thus, between the adjacent bag-like structures, only the substrate is disposed, and ends of the protrusions, which are swaged, are not disposed. Because no portions to be swaged are located between adjacent bag-like structures, the bag-like structure is prevented from being interfered with by swaged portions during inflation and contraction of the bag-like structure. Additionally, the thickness of the plurality of bag-like structures is only added the thickness of the substrate, and thus the thickness of the cuff, constituted by the plurality of bag-like structures, can be prevented from increasing.

Advantageous Effects of Invention

The present invention can provide a blood pressure measurement device that can enhance the joining strength between the cuff and the curler.

BRIEF DESCRIPTION OF DRAWINGS

FIG. 1 is a perspective view illustrating a configuration of a blood pressure measurement device according to a first embodiment of the present invention.

FIG. 2 is a perspective view illustrating the configuration of the blood pressure measurement device.

FIG. 3 is an exploded perspective view illustrating the configuration of the blood pressure measurement device.

FIG. 4 is an explanatory diagram illustrating a state in which the blood pressure measurement device is attached to the wrist.

FIG. 5 is a block diagram illustrating the configuration of the blood pressure measurement device.

FIG. 6 is a perspective view illustrating a configuration of a device body and a curler of the blood pressure measurement device.

FIG. 7 is a plan view illustrating a configuration of a cuff structure of the blood pressure measurement device.

FIG. 8 is a plan view illustrating another configuration of the cuff structure of the blood pressure measurement device.

FIG. 9 is a cross-sectional view illustrating a configuration of a belt, the curler, and the cuff structure of the blood pressure measurement device.

FIG. 10 is a cross-sectional view illustrating the configuration of the curler and the cuff structure of the blood pressure measurement device.

FIG. 11 is a cross-sectional view illustrating the configuration of the curler and the cuff structure of the blood pressure measurement device.

FIG. 12 is a cross-sectional view illustrating the configuration of the curler and the cuff structure of the blood pressure measurement device.

FIG. 13 is an explanatory diagram illustrating the configuration in which the cuff structure is inflated in a state in which the blood pressure measurement device is attached to the wrist.

FIG. 14 is a cross-sectional view illustrating the configuration in which the cuff structure is inflated in a state in which the blood pressure measurement device is attached to the wrist.

FIG. 15 is a plan view illustrating a configuration of a substrate in the blood pressure measurement device.

FIG. 16 is a side view illustrating the configuration of the substrate.

FIG. 17 is a plan view illustrating a configuration of an air bag in the blood pressure measurement device.

FIG. 18 is a plan view illustrating a configuration of a curler in the blood pressure measurement device.

FIG. 19 is a side view illustrating the configuration of the curler.

FIG. 20 is a flowchart illustrating an example of usage of the blood pressure measurement device.

FIG. 21 is a perspective view illustrating an example in which the blood pressure measurement device is attached to the wrist.

FIG. 22 is a perspective view illustrating an example in which the blood pressure measurement device is attached to the wrist.

FIG. 23 is a perspective view illustrating an example in which the blood pressure measurement device is attached to the wrist.

FIG. 24 is an explanatory diagram illustrating an example of junction between the curler and the cuff structure in the blood pressure measurement device.

FIG. 25 is a cross-sectional view illustrating a configuration of the curler and the cuff structure according to a modified example of the present invention.

FIG. 26 is a plan view illustrating a configuration of a substrate according to the modified example of the present invention.

FIG. 27 is a plan view illustrating a configuration of a curler according to the modified example of the present invention.

FIG. 28 is a side view illustrating a configuration of the curler according to the modified example of the present invention.

FIG. 29 is a plan view illustrating a configuration of a substrate according to the modified example of the present invention.

FIG. 30 is a perspective view illustrating a configuration of a blood pressure measurement device according to a second embodiment of the present invention.

FIG. 31 is a cross-sectional view illustrating the configuration of the blood pressure measurement device.

FIG. 32 is a block diagram illustrating the configuration of the blood pressure measurement device.

DESCRIPTION OF EMBODIMENTS

First Embodiment

An example of a blood pressure measurement device 1 according to a first embodiment of the present invention will be described below with reference to FIGS. 1 to 19.

FIG. 1 is a perspective view illustrating a configuration of the blood pressure measurement device 1 according to an embodiment of the present invention in a state in which a belt 4 is closed. FIG. 2 is a perspective view illustrating the configuration of the blood pressure measurement device 1 in a state in which the belt 4 is open. FIG. 3 is an exploded perspective view illustrating the configuration of the blood pressure measurement device 1. FIG. 4 is an explanatory diagram illustrating, in cross section, a state in which the blood pressure measurement device 1 is attached to the wrist 200. FIG. 5 is a block diagram illustrating the configuration of the blood pressure measurement device 1. FIG. 6 is a perspective view illustrating a configuration of a device body 3 and a curler 5 of the blood pressure measurement device 1. FIG. 7 is a plan view illustrating a configuration of a cuff structure 6 of the blood pressure measurement device 1. FIG. 8 is a plan view illustrating another configuration of the cuff structure 6 of the blood pressure measurement device 1. FIG. 9 is a cross-sectional view illustrating a configuration of the belt 4, the curler 5, and the cuff structure 6 on a palm-side cuff 71 side of the blood pressure measurement device 1, which is taken along line IX-IX in FIG. 7. FIG. 10 is a cross-sectional view illustrating a partially omitted configuration of a curler 5 and a cuff structure 6 in the blood pressure measurement device 1. FIG. 11 is a cross-sectional view illustrating the configuration of the curler 5 and the cuff structure 6 on a back-side cuff 74 side of the blood pressure measurement device 1. FIG. 12 is a cross-sectional view illustrating the configuration of the cuff structure 6 with the curler 5 and a tube 92 omitted, on the back-side cuff 74 side of the blood pressure measurement device 1, which is taken along line XI-XI in FIG. 7. FIG. 13 is an explanatory diagram illustrating the configuration in which the cuff structure 6 is inflated in a state in which the blood pressure measurement device 1 attached to the wrist 200. FIG. 14 is a cross-sectional view illustrating the configuration in which the cuff structure 6 is inflated in a state in which the blood pressure measurement device 1 attached to the wrist, which is taken along line XIII-XIII in FIG. 7. FIG. 15 and FIG. 16 are a plan view and a side view illustrating a configuration of a substrate in the blood pressure measurement device 1. FIG. 17 is a plan view illustrating a configuration of air bags 81 and 101 in the blood pressure measurement device 1. FIGS. 18 and 19 are a plan view and a side view illustrating the configuration of the curler 5 in the blood pressure measurement device 1.

The blood pressure measurement device 1 is an electronic blood pressure measurement device attached to a living body. The present embodiment will be described using an electronic blood pressure measurement device having an aspect of a wearable device attached to a wrist 200 of the living body.

As illustrated in FIGS. 1 to 3, the blood pressure measurement device 1 includes a device body 3, a belt 4 that fixes the device body 3 at the wrist, the curler 5 disposed between the belt 4 and the wrist, the cuff structure 6 including a palm-side cuff 71, a sensing cuff 73, and a back-side cuff 74, a fluid circuit 7 fluidly connecting the device body 3 and the cuff structure 6, and a junction means 8 joining the curler 5 and the cuff structure 6.

As illustrated in FIGS. 1 to 5, the device body 3 includes, for example, a case 11, a display unit 12, an operation unit 13, a pump 14, a flow path unit 15, an on-off valve 16, a pressure sensor 17, a power supply unit 18, a vibration motor 19, and a control substrate 20. The device body 3 feeds a fluid to the cuff structure 6 using the pump 14, the on-off valve 16, the pressure sensor 17, the control substrate 20, and the like.

As illustrated in FIGS. 1 to 3, the case 11 includes an outer case 31, a windshield 32 that covers an upper opening of the outer case 31, a base 33 provided at a lower portion of an interior of the outer case 31, and a back lid 35 covering a lower portion of the outer case 31.

The outer case 31 is formed in a cylindrical shape. The outer case 31 includes pairs of lugs 31a provided at respective symmetrical positions in the circumferential direction of an outer circumferential surface, and spring rods 31b each provided between the lugs 31 of each of the two pairs of lugs 31a. The windshield 32 is, for example, a circular glass plate.

The base portion 33 holds the display unit 12, the operation unit 13, the pump 14, the on-off valve 16, the pressure sensor 17, the power supply unit 18, the vibration motor 19, and the control substrate 20. Additionally, the base 33 constitutes a portion of the flow path unit 15 that makes the pump 14 and the cuff structure 6 fluidly continuous.

The back lid 35 covers a living body side end portion of the outer case 31. The back lid 35 is fixed to the living body side end portion of the outer case 31 or the base 33 using, for example, four screws 35a or the like.

The display unit 12 is disposed on the base portion 33 of the outer case 31 and directly below the windshield 32. The display unit 12 is electrically connected to the control board 20. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided on the case 11, a sensor 42 that detects operation of the buttons 41, and a touch panel 43 provided on the display unit 12 or the windshield 32, as illustrated in FIG. 5. When operated by the user, the operation unit 13 converts an instruction into an electrical signal. The sensor 42 and the touch panel 43 are electrically connected to the control substrate 20 to output electrical signals to the control substrate 20.

As the plurality of buttons 41, for example, three buttons are provided. The buttons 41 are supported by the base 33 and protrude from the outer circumferential surface of the outer case 31. The plurality of buttons 41 and a plurality of the sensors 42 are supported by the base 33. The touch panel 43 is integrally provided on the windshield 32, for example.

The pump 14 is, for example, a piezoelectric pump. The pump 14 compresses air and feeds compressed air to the cuff structure 6 through the flow path unit 15. The pump 14 is electrically connected to the control substrate 20.

The flow path unit 15 constitutes a flow path connecting from the pump 14 to the palm-side cuff 71 and the back-side cuff 74 and a flow path connecting from the pump 14 to the sensing cuff 73, as illustrated in FIG. 5. Additionally, the flow path unit 15 constitutes a flow path connecting from the palm-side cuff 71 and the back-side cuff 74 to the atmosphere, and a flow path connecting from the sensing cuff 73 to the atmosphere. The flow path unit 15 is a flow path of air constituted by a hollow portion, a groove, a tube, or the like provided in the base portion 33 and the like.

The on-off valve 16 opens and closes a portion of the flow path 15. A plurality of the on-off valves 16 is provided, for example, as illustrated in FIG. 5, and selectively opens and closes the flow path connecting from the pump 14 to the palm-side cuff 71 and the back-side cuff 74, the flow path connecting from the pump 14 to the sensing cuff 73, the flow path connecting from the palm-side cuff 71 and the back-side cuff 74 to the atmosphere, and the flow path connecting from the sensing cuff 73 to the atmosphere, by the combination of opening and closing of each of the on-off valves 16. For example, two on-off valves 16 are used.

The pressure sensor 17 detects the pressures in the palm-side cuff 71, the sensing cuff 73 and the back-side cuff 74. The pressure sensor 17 is electrically connected to the control substrate 20. The pressure sensor 17 converts a detected pressure into an electrical signal, and outputs the electrical signal to the control substrate 20. The pressure sensor 17 is provided in the flow path connecting from the pump 14 to the palm-side cuff 71 and the back-side cuff 74 and in the flow path connecting from the pump 14 to the sensing cuff 73, as illustrated in FIG. 5. These flow paths are continuous through the palm-side cuff 71, the sensing cuff 73, and the back-side cuff 74, and thus the pressure in these flow paths corresponds to the pressure in the internal space of the palm-side cuff 71, the sensing cuff 73, and the back-side cuff 74.

The power supply unit 18 is, for example, a secondary battery such as a lithium ion battery. The power supply unit 18 is electrically connected to the control substrate 20. The power supply unit 18 supplies power to the control substrate 20.

As illustrated in FIGS. 5 and 6, the control substrate 20 includes, for example, a substrate 51, an acceleration sensor 52, a communication unit 53, a storage unit 54, and a control unit 55. The control substrate 20 is constituted by the acceleration sensor 52, the communication unit 53, the storage unit 54, and the control unit 55 that are mounted on the substrate 51.

The substrate 51 is fixed to the base 33 of the case 11 using screws or the like.

The acceleration sensor 52 is, for example, a 3-axis acceleration sensor. The acceleration sensor 52 outputs, to the control unit 55, an acceleration signal representing acceleration of the device body 3 in three directions orthogonal to one another. For example, the acceleration sensor 52 is used to measure, from the detected acceleration, the amount of activity of a living body to which the blood pressure measurement device 1 is attached.

The communication unit 53 is configured to be able to transmit and receive information to and from an external device wirelessly or by wire. For example, the communication unit 53 transmits information controlled by the control unit 55, and information of a measured blood pressure value, a pulse, and the like to an external device via a network, and receives a program or the like for software update from an external device via a network and sends the program or the like to the control unit 55.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 53 may be configured to include a plurality of wireless antennas, micro-USB connectors, or the like.

The storage unit 54 pre-stores program data for controlling the overall blood pressure measurement device 1 and a fluid circuit 7, settings data for setting various functions of the blood pressure measurement device 1, calculation data for calculating a blood pressure value and a pulse from pressure measured by the pressure sensors 17, and the like. Additionally, the storage unit 54 stores information such as a measured blood pressure value and a measured pulse.

The control unit 55 is constituted by one or more CPUs, and controls operation of the overall blood pressure measurement device 1 and operation of the fluid circuit. The control unit 55 is electrically connected to and supplies power to the display unit 12, the operation unit 13, the pump 14, each of the on-off valves 16 and the pressure sensors 17. Additionally, the control unit 55 controls operation of the display unit 12, the pump 14, and the on-off valves 16, based on electrical signals output by the operation unit 13 and the pressure sensors 17.

For example, as illustrated in FIG. 5, the control unit 55 includes a main Central Processing Unit (CPU) 56 that controls operation of the overall blood pressure measurement device 1, and a sub-CPU 57 that controls operation of the fluid circuit 7. For example, the main CPU 56 obtains measurement results such as blood pressure values, for example, the systolic blood pressure and the diastolic blood pressure, and the heart rate, from electrical signals output by the pressure sensor 17, and outputs an image signal corresponding to the measurement results to the display unit 12.

For example, the sub-CPU 57 drives the pump 14 and the on-off valves 16 to feed compressed air to the palm-side cuff 71 and the sensing cuff 73 when an instruction to measure the blood pressure is input from the operation unit 13. In addition, the sub-CPU 57 controls driving and stopping of the pump 14 and opening and closing of the on-off valves 16 based on electrical signal output by the pressure sensors 17. The sub-CPU 57 controls the pump 14 and the on-off valves 16 to selectively feed compressed air to the palm-side cuff 71 and the sensing cuff 73 and selectively depressurize the palm-side cuff 71 and the sensing cuff 73.

As illustrated in FIGS. 1 to 3, the belt 4 includes a first belt 61 provided on a first pair of lugs 31a and a first spring rod 31b, and a second belt 62 provided on a second pair of lugs 31a and a second spring rod 31b. The belt 4 is wrapped around the wrist 200 with a curler 5 in between.

The first belt 61 is referred to as a so-called a parent and is configured like a band. The first belt 61 includes a first hole portion 61a provided at a first end portion of the first belt 61 and extending orthogonally to the longitudinal direction of the first belt 61, a second hole portion 61b provided at a second end portion of the first belt 61 and extending orthogonally to the longitudinal direction of the first belt 61, and a buckle 61c provided on the second hole portion 61b. The first hole portion 61a has an inner diameter at which the spring rod 31b can be inserted into the first hole portion 61a and at which the first belt 61 can rotate with respect to the spring rod 31b. In other words, the first belt 61 is rotatably held by the outer case 31 by disposing the first hole portion 61a between the pair of lugs 31a and around the spring rod 31b.

The second hole portion 61b is provided at a tip of the first belt 61. The buckle 61c includes a frame body 61d in a rectangular frame shape and a prong 61e rotatably attached to the frame body 61d. A side of the frame body 61d to which the prong 61e is attached is inserted into the second hole portion 61b and the frame body 61d is attached in such a manner as to be rotatable with respect to the first belt 61.

The second belt 62 is referred to as a so-called blade tip, and is configured in a band-like shape having a width at which the second belt 62 can be inserted into the frame body 61d. In addition, the second belt 62 includes a plurality of small holes 62a into which the prong 61e is inserted. Additionally, the second belt 62 includes a third hole portion 62b provided at first end portion of the second belt 62 and extending orthogonally to the longitudinal direction of the second belt 62. The third hole portion 62b has an inner diameter at which the spring rod 31b can be inserted into the third hole portion 62b and at which the second belt 62 can rotate with respect to the spring rod 31b. In other words, the second belt 62 is rotatably held by the outer case 31 by disposing the third hole portion 62b between the pair of lugs 31a and around the spring rod 31b.

Thus, with the second belt 62 inserted into the frame body 61d and with the prong 61e inserted into the small hole 62a, the first belt 61 and the second belt 62 are integrally connected together and thus the belt 4 comes to have an annular shape following along the circumferential direction of the wrist 200 along with the outer case 31.

As illustrated in FIG. 4, the curler 5 is configured in a band-like shape that curves along the circumferential direction of the wrist. The curler 5 is formed with a first end and a second end spaced apart from each other. For example, a first end-side outer surface of the curler 5 is fixed to the back lid 35 of the device body 3. The first end and the second end of the curler 5 are disposed at positions where the first end and the second end protrude from the back lid 35. Furthermore, the first end and the second end of the curler 5 are located adjacent to each other at a predetermined distance from each other.

As a specific example, the curler 5 is fixed to a living body side end portion of the outer case 31 or the base 33 along with the back lid 35 using screws 35a or the like. Additionally, the curler 5 is fixed to the back lid 35 such that the first end and the second end are located on one lateral side of the wrist 200 when the blood pressure measurement device 1 is attached to the wrist 200.

As a specific example, as illustrated in FIG. 1, FIG. 2, and FIG. 4, the curler 5 has a shape that curves along a direction orthogonal to the circumferential direction of the wrist, in other words, along the circumferential direction of the wrist 200 in a side view from the longitudinal direction of the wrist. The curler 5 extends, for example, from the device body 3 through the hand back side of the wrist 200 and one lateral side of the wrist 200 to the hand palm side of the wrist 200 and toward the other lateral side of the wrist 200. Specifically, by curving along the circumferential direction of the wrist 200, the curler 5 is disposed across the most of the wrist 200 in the circumferential direction, with both ends of the curler 5 spaced at a predetermined distance from each other.

Furthermore, a part of the configuration of the junction means 8 is formed in the curler 5. For example, the curler 5 includes a plurality of junction target holes 113 on an outer circumferential edge of the curler 5, the junction target holes 113 constituting the junction means 8 and described later.

The curler 5 has hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist.

The cuff structure 6 is disposed on an inner circumferential surface of the curler 5, and is held along the shape of the inner circumferential surface of the curler 5. As a specific example, the palm-side cuff 71 and the back-side cuff 74 are disposed on the inner circumferential surface of the curler 5, and the palm-side cuff 71 and the back-side cuff 74 are joined with the junction means 8.

The curler 5 is formed of a resin material. The curler 5 is formed of, for example, a thermoplastic resin material, and specifically, polypropylene. The curler 5 is formed, for example, to a thickness of approximately 1 mm.

As illustrated in FIGS. 1 to 4 and 7 to 14, the cuff structure 6 includes the palm-side cuff (cuff) 71, a back plate 72, the sensing cuff 73, and the back-side cuff (cuff) 74. The cuff structure 6 is fixed to the curler 5. The cuff structure 6 includes the palm-side cuff 71, the back plate 72, and the sensing cuff 73 that are stacked one another and disposed on the curler 5, and the back-side cuff 74 that is spaced apart from the palm-side cuff 71, the back plate 72, and the sensing cuff 73 and disposed on the curler 5.

As a specific example, the cuff structure 6 includes the palm-side cuff 71, the back plate 72, the sensing cuff 73, and the back-side cuff 74 that are disposed on an inner surface of the curler 5. The cuff structure 6 is fixed to the inner surface of the curler 5 on the hand palm side of the wrist 200 with the palm-side cuff 71, the back plate 72, and the sensing cuff 73 stacked in this order from the inner surface of the curler 5 toward the living body. In addition, the cuff structure 6 includes the back-side cuff 74 disposed on the inner surface of the curler 5 on the hand back side of the wrist 200. Each of the members of the cuff structure 6 is fixed to an adjacent member of the cuff structure 6 in a stacking direction with a double-sided tape, an adhesive, or the like.

The palm-side cuff 71 is a so-called pressing cuff. The palm-side cuff 71 is fluidly connected to the pump 14 through the flow path unit 15. The palm-side cuff 71 is inflated to press the back plate 72 and the sensing cuff 73 toward the living body side. The palm-side cuff 71 includes a plurality of, for example, two-layer air bags 81, and a plurality of insertion holes 82 provided in the air bag 81 disposed on the curler 5 side that is one of the two-layer air bags 81.

Here, the air bags 81 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags such as liquid bags. The plurality of air bags 81 are stacked and are in fluid communication with one another in the stacking direction.

Each of the air bags 81 is constituted in a rectangular shape that is long in one direction. The air bag 81 is constituted, for example, by combining two sheet members 86 that are long in one direction, and thermally welding edges of the sheet members. In other words, the air bag 81 includes a welded portion 81a corresponding to welded edge portions on four sides of the air bag 81.

As a specific example, as illustrated in FIGS. 7 to 9, the two-layer air bags 81 include a first sheet member 86a, a second sheet member 86b, a third sheet member 86c, and a fourth sheet member 86d in this order from the living body side. The second sheet member 86b constitutes a first-layer air bag 81 along with the first sheet member 86a, the third sheet member 86c is integrally bonded to the second sheet member 86b, and the fourth sheet member 86d constitutes a second-layer air bag 81 along with the third sheet member 86c. Note that the two-layer air bags 81 are integrally constituted by joining each of the sheet members 86 of the adjacent air bags 81 by bonding with a double-sided tape, an adhesive, or the like, or welding or the like.

Edge portions of four sides of the first sheet member 86a are welded to corresponding edge portions of four sides of the second sheet member 86b to constitute the air bag 81. The second sheet member 86b and the third sheet member 86c are disposed facing each other, and each includes a plurality of openings 86b1 and 86cl through which the two air bags 81 are fluidly continuous.

Edge portions of four sides of the third sheet member 86c are welded to corresponding edge portions of four sides of the fourth sheet member 86d to constitute the air bag 81. The welded portion 81a formed along the edge portions of the third sheet member 86c and the fourth sheet member 86d includes a plurality of insertion holes 82. The fourth sheet member 86d is disposed on the curler 5 side.

As illustrated in FIGS. 10, 14, and 17, the plurality of insertion holes 82 are configured such that parts of the junction means 8 can be inserted through the insertion holes 82. In addition, the plurality of insertion holes 82 face the plurality of junction target holes 113 of the curler 5 when the two-layer air bags 81 are disposed on the curler 5. The plurality of insertion holes 82 are provided with spacing predetermined intervals all along the edge portions of the welded portion 81a of the air bag 81 or 101 disposed on the curler 5 side that is one of the six-layer air bags 81 or 101 of the air bag 81 or 101.

In this regard, the predetermined intervals refer to the intervals at which, for example, the air bags 81 of the palm-side cuff 71 can be joined to the curler 5 at a suitable strength, and, for example, in a case where an air flow path to the back-side cuff 74, an air flow path to the sensing cuff 73, or the like is provided in the palm-side cuff 71 or between the palm-side cuff 71 and the curler 5, refer to the intervals at which these flow paths or the like can be arranged, and the predetermined intervals are set as appropriate. Additionally, the predetermined intervals are not limited to equal intervals.

The back plate 72 is applied to an outer surface of the first sheet member 86a of the palm-side cuff 71 with an adhesive layer, a double-sided tape, or the like. The back plate 72 is formed in a plate shape using a resin material. The back plate 72 is made of polypropylene, for example, and is formed into a plate shape having a thickness of approximately 1 mm. The back plate 72 has shape followability.

Here, "shape followability" refers to a function of the backplate 72 by which the back plate 72 can be deformed in such a manner as to follow the shape of a contacted portion of the wrist 200 to be disposed, the contacted portion of the wrist 200 refers to a region of the wrist 200 that is faced by the back plate 72, and the contact as used herein includes both direct contact and indirect contact with the sensing cuff 73 in between.

For example, as illustrated in FIG. 9, the back plate 72 includes a plurality of grooves 72a formed in both main surfaces of the back plate 72 and extending in a direction orthogonal to the longitudinal direction. As illustrated in FIG. 9, a plurality of the grooves 72a are provided in both main surfaces of the back plate 72. The plurality of grooves 72a provided in one of the main surfaces face the corresponding grooves 72a provided in the other main surface in the thickness direction of the back plate 72. Additionally, the plurality of grooves 72a are disposed at equal intervals in the longitudinal direction of the back plate 72.

In the back plate 72, portions including the plurality of grooves 72a are thinner than portions including no grooves 72a and the portions including the plurality of grooves 72a are thus easily deformed. Thus, the back plate 72 deforms following along the shape of the wrist 200 and has shape followability to extend along the circumferential direction of the wrist. The back plate 72 is formed such that the length of the back plate 72 is sufficient to cover the hand palm side of the wrist 200. The back plate 72 transfers the pressing force from the palm-side cuff 71 to the back plate 72 side main surface of the sensing cuff 73 in a state in which the back plate 72 is extending along the shape of the wrist 200.

The sensing cuff 73 is fixed to the living body side main surface of the back plate 72. The sensing cuff 73 is in direct contact with a region of the wrist 200 where an artery 210 resides, as illustrated in FIGS. 9 and 14. The artery 210 as used herein is the radial artery and the ulnar artery. The sensing cuff 73 is formed in the same shape as that of the back plate 72 or a shape that is smaller than that of the back plate 72, in the longitudinal direction and the width direction of the back plate 72. The sensing cuff 73 is inflated to compress a hand palm-side region of the wrist 200 in which the artery 210 resides. The sensing cuff 73 is pressed by the inflated palm-side cuff 71 toward the living body side with the back plate 72 in between.

As a specific example, the sensing cuff 73 includes one air bag 91, a tube 92 that communicates with the air bag 91, and a connection portion 93 provided at a tip of the tube 92. One main surface of the air bag 91 of the sensing cuff 73 is fixed to the back plate 72. For example, the sensing cuff 73 is applied to the living body side main surface of the back plate 72 using a double-sided tape, an adhesive layer, or the like.

Here, the air bag 91 is a bag-like structure, and in the present embodiment, the blood pressure measurement device 1 is configured to use air with the pump 14, and thus the present embodiment will be described using the air bag. However, in a case where a fluid other than air is used, the bag-like structure may be a liquid bag and the like.

The air bag 91 is constituted in a rectangular shape that is long in one direction. The air bag 91 is constituted, for example, by combining two sheet members 96 that are long in one direction, and thermally welding edges of the sheet members. As a specific example, the air bag 91 includes a fifth sheet member 96a and a sixth sheet member 96b in this order from the living body side as illustrated in FIGS. 11 and 14.

For example, the fifth sheet member 96a and the sixth sheet member 96b are fixed by welding, with a tube 92 that is fluidly continuous with the internal space of the air bag 91 being disposed on one side of each of the fifth sheet member 96a and the sixth sheet member 96b. For example, the fifth sheet member 96a and the sixth sheet member 96b are welded together integrally with the tube 92 by welding edge portions of four sides of the fifth sheet member 96a to corresponding edge portions of four sides of the sixth sheet member 96b in a state in which the tube 92 is disposed between the fifth sheet member 96a and the sixth sheet member 96b.

The tube 92 is provided at one longitudinal end portion of the air bag 91. As a specific example, the tube 92 is provided at an end portion of the air bag 91 near the device body 3. The tube 92 includes the connection portion 93 at the tip. The tube 92 is connected to the flow path unit 15 and constitutes a flow path between the device body 3 and the air bag 91. The connection portion 93 is connected to the flow path unit 15. The connection portion 93 is, for example, a nipple.

The back-side cuff 74 is a so-called tensile cuff. The back-side cuff 74 is fluidly connected to the pump 14 through the flow path unit 15. The back-side cuff 74 is inflated to press the curler 5 such that the curler 5 is spaced apart from the wrist 200, pulling the belt 4 and the curler 5 toward the hand back side of the wrist 200. The back-side cuff 74 includes air bags 101 in a plurality of, for example, six layers, a tube 102 in communication with the air bags 101, a connection portion 103 provided at a tip of the tube 102, and a plurality of insertion holes 104 provided in the air bag 101 disposed on the curler 5 side that is one of the six-layer air bags 101.

Additionally, the back-side cuff 74 is configured such that the thickness of the back-side cuff 74 in an inflating direction, in the present embodiment, in the direction in which the curler 5 and the wrist 200 face each other, during inflation, is larger than the thickness of the palm-side cuff 71 in the inflating direction during inflation and the thickness of the sensing cuff 73 in the inflating direction during inflation. Specifically, the air bags 101 of the back-side cuff 74 include more layers than the air bags 81 in the palm-side cuff 71 and the air bag 91 in the sensing cuff 73, and are thicker than the palm-side cuff 71 and the sensing cuff 73 when the air bags 101 are inflated from the curler 5 toward the wrist 200.

Here, the air bag 101 is a bag-like structure, and in the present embodiment, the blood pressure measurement device 1 is configured to use air with the pump 14, and thus the present embodiment will be described using the air bag. However, in a case where a fluid other than air is used, the bag-like structure may be a fluid bag such as a liquid bag. A plurality of the air bags 101 are stacked and are in fluid communication in the stacking direction.

The air bag 101 is constituted in a rectangular shape that is long in one direction. The air bag 101 is constituted, for example, by combining two sheet members 106 that are long in one direction, and thermally welding edges of the sheet members. In other words, the air bag 101 includes a welded portion 101a corresponding to welded edge portions on four sides.

As a specific example, as illustrated in FIGS. 11 and 12, the six-layer air bags 101 include a seventh sheet member 106a, an eighth sheet member 106b, a ninth sheet member 106c, a tenth sheet member 106d, an eleventh sheet member 106e, a twelfth sheet member 106f, a thirteenth sheet member 106g, a fourteenth sheet member 106h, a fifteenth sheet member 106i, a sixteenth sheet member 106j, a seventeenth sheet member 106k, and an eighteenth sheet member 106l in this order from the living body side. Note that the six-layer air bags 101 is integrally constituted by joining each of the sheet members 106 of the adjacent air bags 101 by bonding with a double-sided tape, an adhesive, or the like, or welding or the like.

Edge portions of four sides of the seventh sheet member 106a are welded to corresponding edge portions of four sides of the eighth sheet member 106b to constitute a first-layer air bag 101. The eighth sheet member 106b and the ninth sheet member 106c are disposed facing each other and are integrally bonded together. The eighth sheet member 106*b* and the ninth sheet member 106*c* include a plurality of openings 106*b*1 and 106*c*1 through which the adjacent air bags 101 are fluidly continuous. Edge portions of four sides of the ninth sheet member 106*c* are welded to corresponding edge portions of four sides of the tenth sheet member 106*d* to constitute a second-layer air bag 101.

The tenth sheet member 106*d* and the eleventh sheet member 106*e* are disposed facing each other and are integrally bonded together. The tenth sheet member 106*d* and the eleventh sheet member 106*e* include a plurality of openings 106*d*1 and 106*e*1 through which the adjacent air bags 101 are fluidly continuous. Edge portions of four sides of the eleventh sheet member 106*e* are welded to corresponding edge portions of four sides of the twelfth sheet member 106*f* to constitute a third-layer air bag 101.

The twelfth sheet member 106*f* and the thirteenth sheet member 106*g* are disposed facing each other and are integrally bonded together. The twelfth sheet member 106*f* and the thirteenth sheet member 106*g* include a plurality of openings 106*f*1 and 106*g*1 through which the adjacent air bags 101 are fluidly continuous. Edge portions of four sides of the thirteenth sheet member 106*g* are welded to corresponding edge portions of four sides of the fourteenth sheet member 106*h* to constitute a fourth-layer air bag 101.

The fourteenth sheet member 106*h* and the fifteenth sheet member 106*i* are disposed facing each other and are integrally bonded together. The fourteenth sheet member 106*h* and the fifteenth sheet member 106*i* include a plurality of openings 106*h*1 and 106*i*1 through which the adjacent air bags 101 are fluidly continuous. Edge portions of four sides of the fifteenth sheet member 106*i* are welded to corresponding edge portions of four sides of the sixteenth sheet member 106*j* to constitute a fifth-layer air bag 101.

The sixteenth sheet member 106*j* and the seventeenth sheet member 106*k* are disposed facing each other and are integrally bonded together. The sixteenth sheet member 106*j* and the seventeenth sheet member 106*k* include a plurality of openings 106*j*1 and 106*k*1 through which the adjacent air bags 101 are fluidly continuous. Edge portions of four sides of the seventeenth sheet member 106*k* are welded to corresponding edge portions of four sides of the eighteenth sheet member 106*l* to constitute a sixth-layer air bag 101. The welded portion 101*a* formed on the edge portions of the seventeenth sheet member 106*k* and the eighteenth sheet member 106*l* includes a plurality of the insertion holes 82. The eighteenth sheet member 106*l* is disposed on the curler 5 side.

In addition, for example, a tube 102 that is fluidly continuous with the internal space of the air bag 101 is disposed on one side of the seventeenth sheet member 106*k* and the eighteenth sheet member 106*l*, and is fixed by welding. For example, in a state in which the tube 102 is disposed between the seventeenth sheet member 106*k* and the eighteenth sheet member 106*l*, the edge portions of the seventeenth sheet member 106*k* are welded to the edge portions of the eighteenth sheet member 106*l* in a rectangular frame shape to form the air bag 101. Thus, the tube 102 is integrally welded to the air bag 101.

For example, the sixth-layer air bag 101 as described above is constituted integrally with the second layer air bag 81 of the palm-side cuff 71. Specifically, the seventeenth sheet member 106*k* is constituted integrally with the third sheet member 86*c*, and the eighteenth sheet member 106*l* is constituted integrally with the fourth sheet member 86*d*.

In more detail, the third sheet member 86*c* and the seventeenth sheet member 106*k* constitute a rectangular sheet member that is long in one direction, and the eighteenth sheet member 106*l* and the fourth sheet member 86*d* constitute a rectangular sheet member that is long in one direction. Then, these sheet members are stacked one another, and welding is performed such that first end portion side is welded in a rectangular frame shape, whereas a part of one side on the second end portion side is not welded. Thus, the second-layer air bag 81 of the palm-side cuff 71 is constituted. Then, welding is performed such that the second end portion side is welded in a rectangular frame shape, whereas a part of one side on the first end portion side is not welded. Thus, the sixth-layer air bag 101 in the back-side cuff 74 is constituted. In addition, a part of one side on the facing side of each of the second-layer air bag 81 and the sixth-layer air bag 101 is not welded, and thus the second-layer air bag 81 and the sixth-layer air bag 101 are fluidly continuous.

The tube 102 is connected to one air bag 101 of the six-layer air bags 101 and is provided at one longitudinal end portion of the air bag 101. As a specific example, the tube 102 is provided on the curler 5 side of the six-layer air bags 101 and is provided at the end portion close to the device body 3. The tube 102 includes a connection portion 103 at the tip. The tube 102 constitutes a flow path included in the fluid circuit 7 and located between the device body 3 and the air bags 101. The connection portion 103 is, for example, a nipple.

Note that, as described above, in the present embodiment, the configuration has been described in which a part of the back-side cuff 74 is formed integrally with the palm-side cuff 71 and is fluidly continuous with the palm-side cuff 71. However, no such limitation is intended. For example, as illustrated in FIG. 8, the back-side cuff 74 may be constituted separately from the palm-side cuff 71 and may be fluidly discontinuous with the palm-side cuff 71. For such a configuration, the palm-side cuff 71 may be configured such that, like the sensing cuff 73 and the back-side cuff 74, the palm-side cuff 71 is further provided with a tube and a connection portion, and in the fluid circuit 7 as well, the palm-side cuff 71 is connected to a flow path through which the fluid is fed to the palm-side cuff 71, a check valve, and a pressure sensor.

The plurality of insertion holes 104 are configured such that parts of the junction means 8 can be inserted through the insertion holes 104. Additionally, when the six-layer air bags 101 are disposed on the curler 5, the plurality of insertion holes 104 face the plurality of junction target holes 113 in the curler 5. The plurality of insertion holes 104 are provided with spacing predetermined intervals all along the edge portions of the welded portion 101*a* of the air bag 101 disposed on the curler 5 side that is one of the six-layer air bags 101 of the air bag 101.

In this regard, the predetermined intervals refer to the intervals at which, for example, the back-side cuff 74 can be joined to the curler 5 at a suitable strength, and, for example, in a case where an air flow path to the palm-side cuff 71, an air flow path to the sensing cuff 73, or the like is provided in the back-side cuff 74 or between the back-side cuff 74 and the curler 5, refer to the intervals at which these flow paths or the like can be arranged, and the predetermined intervals are set as appropriate. Additionally, the predetermined intervals are not limited to equal intervals.

Additionally, each of the sheet members 86, 96, and 106 forming the palm-side cuff 71, the sensing cuff 73, and the back-side cuff 74 are formed of a thermoplastic resin material. The thermoplastic resin material is a thermoplastic elastomer. Examples of thermoplastic resin material constituting the sheet members 86, 96, and 106 include thermoplastic polyurethane based resin (hereinafter referred to as TPU), polyvinyl chloride resin, ethylene-vinyl acetate resin, thermoplastic polystyrene based resin, thermoplastic polyolefin resin, thermoplastic polyester based resin, and thermoplastic polyamide resin.

For example, the sheet members 86, 96, and 106 are formed using a molding method such as T-die extrusion molding or injection molding. After being molded by each molding method, the sheet members 86, 96, and 106 are sized into predetermined shapes, and the sized individual pieces are joined by welding or the like to constitute bag-like structures 81, 91, and 101. A high frequency welder or laser welding is used as the welding method.

The fluid circuit 7 is constituted by the case 11, the pump 14, the flow path unit 15, the on-off valves 16, the pressure sensors 17, the palm-side cuff 71, the sensing cuff 73, and the back-side cuff 74. A specific example of the fluid circuit 7 will be described below with two on-off valves 16 that are used in the fluid circuit 7 being designated as a first on-off valve 16A and a second on-off valve 16B, and two pressure sensors 17 that are used in the fluid circuit 17 being designated as a first pressure sensor 17A and a second pressure sensor 17B.

As illustrated in FIG. 5, the fluid circuit 7 includes, for example, a first flow path 7a that makes the palm-side cuff 71 and the back-side cuff 74 continuous with the pump 14, a second flow path 7b constituted by branching from a middle portion of the first flow path 7a and making the sensing cuff 73 continuous with the pump 14, and a third flow path 7c connecting the first flow path 7a to the atmosphere. Additionally, the first flow path 7a includes the first pressure sensor 17A. The first on-off valve 16A is provided between the first flow path 7a and the second flow path 7b. The second flow path 7b includes a second pressure sensor 17B. The second on-off valve 16B is provided between the first flow path 7a and the third flow path 7c.

In the fluid circuit 7 as described above, the first on-off valve 16A and the second on-off valve 16B are closed to connect only the first flow path 7a to the pump 14, and the pump 14 and the palm-side cuff 71 are fluidly connected. In the fluid circuit 7, the first on-off valve 16A is opened and the second on-off valve 16B is closed to connect the first flow path 7a and the second flow path 7b, thus fluidly connecting the pump 14 and the back-side cuff 74, the back-side cuff 74 and the palm-side cuff 71, and the pump 14 and the sensing cuff 73. In the fluid circuit 7, the first on-off valve 16A is closed and the second on-off valve 16B is opened to connect the first flow path 7a and the third flow path 7c, fluidly connecting the palm-side cuff 71, the back-side cuff 74, and the atmosphere together. In the fluid circuit 7, the first on-off valve 16A and the second on-off valve 16B are opened to connect the first flow path 7a, the second flow path 7b, and the third flow path 7c, fluidly connecting the palm-side cuff 71, the sensing cuff 73, the back-side cuff 74, and the atmosphere together.

As illustrated in FIG. 10, the junction means 8 abuts a wrist 200-side surface of the welded portion 81a and 101a of the air bag 81 and 101 disposed adjacent to the curler 5, and parts of the configuration are inserted into the plurality of insertion holes 82 in the welded portion 81a and 101a. The junction means 8 joins the air bags 81 and 101 to the curler 5.

As a specific example, as illustrated in FIGS. 10 to 19, the junction means 8 includes a substrate 111, a plurality of protrusions 112 provided on at least one of the curler 5 and the substrate 111, and a plurality of junction target holes 113 provided in at least one of the substrate 111 and the curler 5.

The present embodiment will be described below using an example in which the plurality of protrusions 112 are provided on the substrate 111 and in which the plurality of junction target holes 113 are provided in the curler 5.

As illustrated in FIGS. 10 and 14, the substrate 111 is provided in each of the palm-side cuff 71 and the back-side cuff 74. As illustrated in FIGS. 15 and 16, the substrate 111 is configured to have a thin plate shape and also have a rectangular frame shape that is substantially the same as the surface shape of the welded portion 81a and 101a of the air bag 81 and 101.

Note that in a case of a configuration in which the palm-side cuff 71 and the back-side cuff 74 are formed being integrally continuous, the configuration may include only one substrate 111 to be provided. In other words, in a case of configuration in which the palm-side cuff 71 and the back-side cuff 74 are formed being integrally continuous, the substrate 111 may have a rectangular frame shape that is substantially the same as a surface shape corresponding to an integral combination of the welded portions 81a and 101a of air bags 81 and 101 constituting the curler 5 side of the palm-side cuff 71 and the back-side cuff 74.

The substrate 111 abuts a wrist 200-side surface of the welded portions 81a and 101a of the air bag 81 and 101 adjacent to the curler 5.

As illustrated in FIG. 12 and FIG. 14, the plurality of protrusions 112 are provided on the surface of the substrate 111 abutting the wrist 200-side surface of the welded portion 81a and 101a of the air bag 81 and 101 adjacent to the curler 5. The plurality of protrusions 112 are provided on the substrate 111 at the same arrangement as those of the plurality of insertion holes 82 and 104 provided in the welded portion 81a and 101a of the air bag 81 and 101. The plurality of protrusions 112 are integrally formed on the substrate 111 by resin molding. The height of the protrusions 112 from the substrate 111 is set being larger than the sum of the thickness of the two sheet members 86 or 106 and the thickness of the curler 5.

The substrate 111 and the plurality of protrusions 112 as described above include a thermoplastic resin material, for example, a material similar to that of the curler 5. As a specific example, the substrate 111 and the plurality of protrusions 112 include polypropylene.

As illustrated in FIG. 12, FIG. 18, and FIG. 19, the plurality of junction target holes 113 are provided at portions where the air bags 81 and 101 of the curler 5 are provided. The plurality of junction target holes 113 are provided in the curler 5 at the same arrangement as those of the plurality of insertion holes 82 and 104 provided in the welded portion 81a and 101a of the air bag 81 and 101.

Next, an example of measurement of a blood pressure value using the blood pressure measurement device 1 will be described using FIGS. 20 to 23. FIG. 20 is a flowchart illustrating an example of a blood pressure measurement using the blood pressure measurement device 1, illustrating both the operation of a user and the operation of the control unit 55. Additionally, FIGS. 21 to 23 illustrate an example of the user wearing the blood pressure measurement device 1 on the wrist 200.

First, the user attaches the blood pressure measurement device 1 to the wrist 200 (step ST1). As a specific example, for example, the user inserts one of the wrists 200 into the curler 5, as illustrated in FIG. 21.

At this time, in the blood pressure measurement device 1, the device body 3 and the sensing cuff 73 are disposed at opposite positions in the curler 5, and thus the sensing cuff 73 is disposed in a region on the hand palm side of the wrist 200 in which the artery 210 resides. Thus, the device body 3 and the back-side cuff 74 are disposed on the hand back side of the wrist 200. Then, as illustrated in FIG. 22, the user passes the second belt 62 through the frame body 61d of the buckle 61c of the first belt 61 with the hand opposite to the hand on which the blood pressure measurement device 1 is disposed. The user then pulls the second belt 62 to bring the member on the inner circumferential surface side of the curler 5, that is, the cuff structure 6, into close contact with the wrist 200, and inserts the prong 61e into the small hole 62a. Thus, as illustrated in FIG. 23, the first belt 61 and the second belt 62 are connected, and the blood pressure measurement device 1 is attached to the wrist 200.

Then, the user operates the operation unit 13 to input an instruction corresponding to the start of measurement of the blood pressure value. The operation unit 13, on which an input operation of the instruction has been performed, outputs an electrical signal corresponding to the start of the measurement to the control unit 55 (step ST2). The control unit 55 receives the electrical signal, and then for example, opens the first on-off valve 16A, closes the second on-off valve 16B, and drives the pump 14 to feed compressed air to the palm-side cuff 71, the sensing cuff 73, and the back-side cuff 74 through the first flow path 7a and the second flow path 7b (step ST3). Thus, the palm-side cuff 71, the sensing cuff 73, and the back-side cuff 74 start to be inflated.

The first pressure sensor 17A and the second pressure sensor 17B detect the pressures in the palm-side cuff 71, the sensing cuff 73, and the back-side cuff 74, and outputs, to the control unit 55, electrical signals corresponding to the pressures (step ST4). Based on the received electrical signals, the control unit 55 determines whether the pressures in the internal spaces of the palm-side cuff 71, the sensing cuff 73, and the back-side cuff 74 have reached a predetermined pressure for measurement of the blood pressure (step ST5). For example, in a case where the internal pressures of the palm-side cuff 71 and the back-side cuff 74 have not reached the predetermined pressure and the internal pressure of the sensing cuff 73 has reached the predetermined pressure, the control unit 55 closes the first on-off valve 16A and feeds compressed air through the first flow path 7a.

When the internal pressures of the palm-side cuff 71 and the back-side cuff 74 and the internal pressure of the sensing cuff 73 all have reached the predetermined pressure, the control unit 55 stops driving the pump 14 (YES in step ST5). At this time, as illustrated in FIGS. 13 and 14, the palm-side cuff 71 and the back-side cuff 74 are sufficiently inflated, and the inflated palm-side cuff 71 presses the back plate 72. Additionally, the back-side cuff 74 presses against the curler 5 in a direction away from the wrist 200, and then the belt 4, the curler 5, and the device body 3 move in a direction away from the wrist 200, and as a result, the palm-side cuff 71, the back plate 72, and the sensing cuff 73 are pulled toward the wrist 200 side.

In addition, when the belt 4, the curler 5, and the device body 3 move in a direction away from the wrist 200 due to the inflation of the back-side cuff 74, the belt 4 and the curler 5 move toward both lateral sides of the wrist 200, and the belt 4, the curler 5, and the device body 3 move in a state of close contact with both lateral sides of the wrist 200. Thus, the belt 4 and the curler 5, which are in close contact with the skin of the wrist 200, pull the skin on both lateral sides of the wrist 200 toward the hand back side. Note that the curler 5 may be configured to indirectly contact the skin of the wrist 200 with the sheet members 86 or 106 in between, for example, as long as the curler 5 can pull the skin of the wrist 200.

Further, the sensing cuff 73 is inflated by being fed with a predetermined amount of air such that the internal pressure equals the pressure required to measure blood pressure, and is pressed toward the wrist 200 by the back plate 72 that is pressed by the palm-side cuff 71. Thus, the sensing cuff 73 presses the artery 210 in the wrist 200 and occludes the artery 210 as illustrated in FIG. 14.

Additionally, the control unit 55, for example, controls the second on-off valve 16B and repeats the opening and closing of the second on-off valve 16B, or adjusts the degree of opening of the second on-off valve 16B to pressurize the internal space of the palm-side cuff 71. In the process of pressurization, based on the electrical signal output by the second pressure sensor 17B, the control unit 55 obtains measurement results such as blood pressure values, for example, the systolic blood pressure and the diastolic blood pressure, and the heart rate and the like (step ST6). The control unit 55 outputs an image signal corresponding to the obtained measurement results to the display unit 12, and displays the measurement results on the display unit 12 (step ST7). In addition, after the end of the blood pressure measurement, the control unit 55 opens the first on-off valve 16A and the second on-off valve 16B.

The display unit 12 receives the image signal, and then displays the measurement results on the screen. The user views the display unit 12 to confirm the measurement results. After the measurement is complete, the user removes the prong 61e from the small hole 62a, removes the second belt 62 from the frame body 61d, and removes the wrist 200 from the curler 5, thus removing the blood pressure measurement device 1 from the wrist 200.

Now, an example of junction between the curler 5 and the cuff structure 6 using the junction means 8 as described above will be described with reference to FIG. 24.

First, the air bags 81 and 101 and the substrate 111 are assembled (step ST11). As a specific example, first, the substrate 111 is disposed between the first-layer air bag 81 and 101 and the second-layer air bag 81 and 101 on the curler 5 side, and the plurality of protrusions 112 are inserted into the plurality of insertion holes 82 and 104. Note that a double-sided tape for temporarily fixing the air bags 81 and 101 to the curler 5 may be applied to the sheet members 86d and 106l of the air bags 81 and 101 in advance. Then, the assembled air bags 81 and 101 and substrate 111 are assembled to the curler 5 (step ST12). As a specific example, the air bags 81 and 101 to which the substrate 111 is integrally assembled are disposed on the inner circumferential surface of the curler 5, and the plurality of protrusions 112 are inserted into the plurality of junction target holes 113.

Then, the tips of the protrusions 112 protruding from the curler 5 are performed swaging processing using a swaging device 300 or the like (step ST13). The swaging device 300 includes, for example, a heating device 300a heating tips of the protrusions 112 and a holding member 300b holding the substrate 111. Swaging processing is performed, for example, using the heating device 300a and the holding member 300b. With the curler 5 and the substrate 111 pressed in a direction to approach each other, tips of the plurality of protrusions 112 are heated and each formed into a predetermined shape using the heating device 300. Thus, the tips of the plurality of protrusions 112 are swaged. In addition, the heating device 300a is used to, for example, heat the peripheries of the junction target holes 113 to weld the protrusions 112 and the peripheries of the junction target holes 113.

These steps mechanically join the substrate 111 and the curler 5 in a state in which the air bags 81 and 101 are included therebetween, as illustrated in FIGS. 10 and 11. Thus, the air bags 81 and 101 are pressed toward the curler 5 side by the substrate 111, and the air bags 81 and 101 are joined to the curler 5.

In the blood pressure measurement device 1 configured as described above according to one embodiment, the curler 5 and the substrate 111 are provided with the plurality of protrusions 112 inserted into the plurality of insertion holes 82 and 104, and the plurality of junction target holes 113 to which the plurality of protrusions 112 are joined. Then, the air bags 81 and 101 are disposed between the curler 5 and the substrate 111, and the protrusions 112 protruding from the junction target holes 113 are performed swaging processing to mechanically join the curler 5 and the substrate 111. Thus, the air bags 81 and 101 can be firmly joined to the curler 5, and thus the blood pressure measurement device 1 can enhance the joining strength between the cuff structure 6 and the curler 5.

In addition, the air bag 81 and 101 is formed by welding the two sheet members 86 and 106, and the welded portion 81a and 101a obtained by welding the two sheet members 86 and 106 is provided with the insertion holes 82 and 104 through which the plurality of protrusions 112 of the junction means 8 are inserted. Thus, the welded portions 81a and 101a can be used as junction margins. This configuration eliminates a need to provide a separate junction margin for joining the air bags 81 and 101 to the curler 5, enabling the blood pressure measurement device 1 to be miniaturized.

In addition, the substrate 111 has a thin plate shape disposed facing the welded portion 81a and 101a and also has a rectangular frame shape that is substantially the same as the shape of the welded portion 81a and 101a of the air bag 81 and 101. Thus, when the air bags 81 and 101 are inflated and contracted, the air bags 81 and 101 are prevented from interfering with the portion to be inflated. Furthermore, the plurality of protrusions 112 are provided on the substrate 111, and thus the swaged tips of the protrusions 112 are located on the outer circumferential surface of the curler 5. Thus, the swaged portions of the protrusions 112 are prevented from interfering with the inflected portions of the air bags 81 and 101.

Accordingly, the cuff structure 6 may be suitably inflected. Additionally, even with the junction means 8, at the time of contraction, the thickness of the cuff structure 6 increases only by an amount equal to the thickness of the substrate 111. This prevents the dimension of the blood pressure measurement device 1 from increasing in the thickness direction. In addition, swaging of the protrusions 112 can be performed from the outer circumferential surface side of the curler 5, and thus a mold and the like of the swaging device is easily disposed, leading to easy manufacturing.

Additionally, the protrusions 112 are formed of a thermoplastic resin material and are thermally swaged, and thus swaging of the protrusions 112 is facilitated. In addition, since the curler 5 and the substrate 111 are formed of a thermoplastic resin material, when the protrusions 112 are thermally swaged, the peripheries of the junction target holes 113 are also heated, and welding of the protrusions 112 and the peripheries of the junction target holes 113 are also achieved during the swaging processing. Thus, the curler 5 and the substrate 111 are joined by welding of the protrusions 112 and the peripheries of the junction target holes 113 as well as by swaging of the protrusions 112, enhancing the joining strength between the curler 5 and the substrate 111. As a result, the joining strength between the curler 5 and the air bags 81 and 101 is enhanced.

Furthermore, as an example in which the curler 5, the substrate 111, and the plurality of protrusions 112 are formed of a thermoplastic resin material, the curler 5, the substrate 111, and the plurality of protrusions 112 are configured to be formed of polypropylene as a similar material. In this regard, "similar materials" refer to two materials that are highly compatible with each other in thermal welding and that have the same softening temperature or close softening temperatures. "Compatibility" refers to the degree of mixing of the resin materials softened or melted during welding, and "high compatibility" means that junction can be achieved in which the resin materials softened or melted during welding mix together at a suitable degree, that is, junction can be achieved at a required junction strength. By constituting the curler 5, the substrate 111, and the plurality of protrusions 112 with the similar materials, the protrusions 112 and the peripheries of the junction target holes 113 can suitably mix during welding, and the joining strength can be further increased.

As described above, the blood pressure measurement device 1 according to the present embodiment enables the joining strength between the curler 5 and the cuff structure 6 to be enhanced.

Note that the present invention is not limited to the embodiments described above. In the example described above, the curler 5, the substrate 111, and the plurality of protrusions 112 are configured to be formed of thermoplastic resin materials that are similar materials. However, no such limitation is intended. For example, the thermoplastic resin materials constituting the curler 5, the substrate 111, and the plurality of protrusions 112 need not be similar materials. However, preferably, in order to more firmly join the cuff structure 6 to the curler 5, the curler 5, the substrate 111, and the plurality of protrusions 112 include similar materials, the protrusions 112 are swaged, and the protrusions 112 and the peripheries of the junction target holes 113 are welded.

Additionally, in the example described above, the curler 5 and the substrate 111 are formed separately. However, no such limitation is intended. For example, as in the blood pressure measurement device 1 according to a modified example illustrated in FIG. 25, the curler 5 and the substrate 111 may be configured to be connected by a hinge portion 114 that is integrally formed on one side of an edge of each of the curler 5 and the substrate 111. By connecting the curler 5 and the substrate 111 by the hinge portion 114 in this way, the curler 5 and the substrate 111 can be molded integrally by resin molding. Thus, manufacturing is facilitated, and the number of parts can be reduced. Furthermore, the curler 5 and the substrate 111 can be rotated around the hinge portion 114 to make the curler 5 and the substrate 111 face each other. This eliminates a need for alignment between the plurality of protrusions 112 and the plurality of junction target holes 113, facilitating assembly of the curler 5, the air bags 81 and 101, and the substrate 111.

In the example described above, as illustrated in FIG. 26, the substrate 111 may be constituted by a plurality of members 111a obtained by division in the longitudinal direction. When the frame-shaped substrate 111 thus includes the plurality of members 111a, even in a case where, for example, a plurality of the air bags 81 and 101 are stacked, the substrate 111 can easily be disposed between the adjacent air bags 81 and 101.

Furthermore, for example, the junction means 8 are not limited to the examples described above. In other words, the junction means 8 may have any other configuration as long as the junction means 8 can abut the wrist 200-side surface of the welded portion 81a and 101a of the air bag 81 and 101 disposed adjacent to the curler 5, and in a state in which the air bags 81 and 101 are pressed toward the curler 5, the curler 5 and the air bags 81 and 101 can be joined. For example, the junction means 8 may include rivets or sewing threads that are used to join the air bags 81 and 101 to the curler 5.

Additionally, the insertion holes 82 and 104 and the junction target hole 113 are not limited to the examples described above. For example, when the curler 5 and the cuff structure 6 are joined with the junction means 8, the insertion holes 82 and 104 and the junction target holes 113 may be formed by perforating the curler 5 and the cuff structure 6.

For example, as in the modified example described above, in a case where the curler 5 and the cuff structure 6 are joined using a rivet or sewing thread as the junction means 8, the insertion holes 82 and 104, and the junction target holes 113 may be configured to be opened in the curler 5 and the cuff structure 6 immediately prior to inserting the junction means 8.

As a specific example, the configuration may be such that the tips of the rivets may be formed sharp enough to puncture the curler 5 and cuff structure 6 to open the insertion holes 82 and 104 and the junction target holes 113 while simultaneously disposing the rivets on the curler 5 and cuff structure 6. Furthermore, as a specific example, the configuration may be such that a threaded sewing needle is used to puncture and sew the curler 5 and the cuff structure 6 to join the curler 5 and the cuff structure 6 with a thread, as a result the insertion holes 82 and 104 and the junction target holes 113 are provided.

In addition, the configuration may be such that the curler 5 is provided with the junction target holes 113 in advance, and the cuff structure 6, which is shaped like a sheet and perforated more easily than the curler 5, is exclusively perforated during manufacturing using the junction means 8 or any other member.

Additionally, for example, a portion of the curler 5 facing the back lid 35 may have the same shape as the surface shape of the back lid 35, as in the modified examples illustrated in FIGS. 27 to 29. When the curler 5 has the same shape as the surface shape of the back lid 35, fixation of the curler 5 to the back lid 35 is facilitated.

Additionally, when a part of the curler 5 is configured as described above, the sheet members 86d and 106l of the air bags 81 and 101 facing the curler 5 and the substrate 111 may have the same shape as the outer shape of the curler 5. In addition, the configuration may be such that, in a portion of the curler 5 facing the back lid 35, the curler 5 is provided with the protrusions 112 instead of the junction target holes 113, and the junction target holes 113 is provided at portions of the substrate 111 facing the protrusions 112 of the curler 5, as illustrated in FIGS. 28 and 29.

The air bags 81 and 101 are not inflated at the outer circumferential edge of a portion of the curler 5 that is formed having the same diameter as the shape of the back lid 35, and thus even in a case where the swaged portions of the protrusions 112 are disposed on the wrist 200 side, the tips of the protrusions 112 are prevented from interfering with the cuff structure 6 when the cuff structure 6 is inflated. In addition, the tips of the protrusions 112 are prevented from being located on the outer circumferential surface side facing the back lid 35, and thus when the curler 5 abuts the back lid 35, the tips of the protrusions 112 are prevented from being disposed between the curler 5 and the back lid 35, allowing the curler 5 and the back lid 35 to come into close contact with each other.

For example, the timings when the first on-off valve 16A and the second on-off valve 16B are opened and closed during blood pressure measurement by the blood pressure measurement device 1 are not limited to the timings in the examples described above, and can be set as appropriate. Additionally, although the example has been described in which the blood pressure measurement device 1 performs blood pressure measurement by calculating the blood pressure with the pressure measured during the process of pressurizing the palm-side cuff 71, no such limitation is intended and the blood pressure may be calculated during the depressurization process or during both the pressurization process and the depressurization process.

In addition, in the example described above, the configuration has been described in which the air bag 81 is formed by each of the sheet members 86, but no such limitation is intended, and for example, the air bag 81 may further include any other configuration in order to manage deformation and inflation of the palm-side cuff 71, for example.

Additionally, in the examples described above, the configuration is described in which the back plate 72 includes the plurality of grooves 72a, but no such limitation is intended. For example, for management of the likelihood of deformation and the like, the number, the depth, and the like of the plurality of grooves 72a may be set as appropriate, and the back plate 72 may be configured to include a member that suppresses deformation.

Furthermore, in the example described above, the blood pressure measurement device 1 has been described using an example of a wearable device attached to the wrist 200, but no such limitation is intended. For example, the blood pressure measurement device may be a blood pressure measurement device 1A wrapped around the upper arm to measure the blood pressure. Hereinafter, as a second embodiment, the blood pressure measurement device 1A will be described with reference to FIG. 30. Note that components in the present embodiment that are similar to the corresponding components of the blood pressure measurement device 1 according to the first embodiment described above are denoted by the same reference signs in the description, and descriptions and illustrations of these components are omitted as appropriate.

For example, as illustrated in FIGS. 30 to 32, the blood pressure measurement device 1A in the second embodiment includes a device body 3A and a cuff structure 6A. The device body 3A includes, for example, a case 11A, the display unit 12, the operation unit 13, the pump 14, the flow path unit 15, the on-off valves 16, the pressure sensors 17, the power supply unit 18, and the control substrate 20. As illustrated in FIG. 32, the device body 3A includes one of each of the pump 14, the on-off valves 16, and the pressure sensors 17.

The case 11A is constituted, for example, in a box shape. The case 11A includes an attachment portion 11a that fixes the cuff structure 6A. The attachment portion 11a is an opening provided in a back surface of the case 11A, for example.

As illustrated in FIGS. 30 to 32, the cuff structure 6A includes a curler 5A constituted by a thermoplastic resin material, a pressing cuff 71A provided on the living body side of the curler 5A and constituted by a thermoplastic resin material, a bag-like cover body 76 inside which the curler 5A and the pressing cuff 71A are disposed and which includes a cloth or the like, and the junction means 8 mechanically joining the curler 5A and the pressing cuff 71A. The cuff structure 6A is wrapped around the upper arm.

The curler 5 includes the protrusions 112 fixed to the attachment portion 11a, for example.

The pressing cuff 71A includes an air bag 81A, a plurality of insertion holes 82 provided in the air bag 81A, and a tube provided to the air bag 81A and fluidly connected to the flow path unit 15. The pressing cuff 71A is housed in the bag-like cover body 76 together with the curler 5A, and is joined to the inner surface of the curler 5A by thermal welding.

Each of the air bags 81A is constituted in a rectangular shape that is long in one direction. The air bag 81A includes the welded portion 81a, for example, by combining two sheet members 86 that are long in one direction, and thermally welding edges of the sheet members 86. As a specific example, the air bag 81A includes a first sheet member 86a and a second sheet member 86b in this order from the living body side. The second sheet member 86b constitutes the air bag 81 along with the first sheet member 86a.

In the blood pressure measurement device 1A, in a state in which the welded portion 81a of the air bag 81A is disposed between the curler 5A and the substrate 111, the curler 5 and the substrate 111 are mechanically joined to join the air bang 81A to the curler 5, as is the case with the blood pressure measurement device 1 described above.

Like the blood pressure measurement device 1 according to the first embodiment described above, the blood pressure measurement device 1A configured as described above can be miniaturized and can stably perform highly accurate blood pressure measurement for a long period of time.

In other words, the embodiments described above are merely examples of the present invention in all respects. Of course, various modifications and variations can be made without departing from the scope of the present invention. Thus, specific configurations in accordance with an embodiment may be adopted as appropriate at the time of carrying out the present invention.

Note that the present invention is not limited to the embodiment, and various modifications can be made in an implementation stage without departing from the gist. Further, embodiments may be carried out as appropriate in a combination, and combined effects can be obtained in such case. Further, the various inventions are included in the embodiment, and the various inventions may be extracted in accordance with combinations selected from the plurality of disclosed constituent elements. For example, in a case where the problem can be solved and the effects can be obtained even when some constituent elements are removed from the entire constituent elements given in the embodiment, the configuration obtained by removing the constituent elements may be extracted as an invention.

REFERENCE SIGNS LIST 1, 1A Blood Pressure measurement device
3, 3A Device body
4 Belt
5, 5A Curler
6, 6A Cuff structure
7 Fluid circuit
7a First flow path
7b Second flow path
7c Third flow path
8 Junction means
11, 11A Case
11a Attachment portion
12 Display unit
13 Operation unit
14 Pump
15 Flow path unit
16 On-off valve
16A First on-off valve
16B Second on-off valve
17 Pressure sensor
17A First pressure sensor
17B Second pressure sensor
18 Power supply unit
19 Vibration motor
20 Control substrate
31 Outer case
31a Lug
31b Spring rod
32 Windshield
33 Base
35 Back lid
35a Screw
41 Button
42 Sensor
43 Touch panel
51 Substrate
52 Acceleration sensor
53 Communication unit
54 Storage unit
55 Control unit
56 Main CPU
57 Sub-CPU
61 First belt
61a First hole portion
61b Second hole portion
61c Buckle
61d Frame body
61e Prong
62 Second belt
62a Small hole
62b Third hole portion
71 Palm-side cuff (cuff)
71A Pressing cuff
72 Back plate
72a Groove
73 Sensing cuff
74 Back-side cuff (cuff)
76 Bag-like cover body
81, 81A Air bag (bag-like structure)
81a Welded portion
82 Insertion hole
86 Sheet member
86a First sheet member
86b Second sheet member
86b1 Opening
86c Third sheet member
86c1 Opening
86d Fourth sheet member
91 Air bag (bag-like structure)
92 Tube
93 Connection unit
96 Sheet member
96a Fifth sheet member
96b Sixth sheet member
101 Air bag (bag-like structure)
101a Welded portion
102 Tube 103 Connection portion
104 Insertion hole
96 Sheet member
106a Seventh sheet member
106b Eighth sheet member
106b1 Opening
106c Ninth sheet member
106c1 Opening
106d Tenth sheet member
106d1 Opening
106e Eleventh sheet member
106e1 Opening
106f Twelfth sheet member
106f1 Opening
106g Thirteenth sheet member
106g1 Opening
106h Fourteenth sheet member
106h1 Opening
106i Fifteenth sheet member
106i1 Opening
106j Sixteenth sheet member
106j1 Opening
106k Seventeenth sheet member
106k1 Opening
106l Eighteenth sheet member
111 Substrate
111 Member
112 Protrusion
113 Junction target hole
114 Hinge portion
200 Wrist
210 Artery
300 Swaging device
300a Heating device
300b Holding member

The invention claimed is:

1. A blood pressure measurement device comprising:
a curler configured to curve to follow a circumferential direction of a portion of a living body where the blood pressure measurement device is attached;
a bag-like structure including two sheet members and a welded portion formed by welding edges of the two sheet members, the welded portion including a plurality of insertion holes, and the bag-like structure being configured to be inflated with a fluid and being disposed on an inner circumferential surface of the curler; and
a junction means abutting a surface on a living body side of the welded portion and inserted into the plurality of insertion holes to join the welded portion to the curler, wherein the junction means includes
a substrate having a frame-shape and being disposed facing the welded portion,
a plurality of protrusions each integrally formed on one of the curler or the substrate, the plurality of protrusions being inserted into the plurality of insertion holes, and
a plurality of junction target holes each formed in one of the substrate or the curler, each of the plurality of protrusions formed on one of the curler or the substrate being inserted and joined to a corresponding one of the plurality of junction target holes formed in another of the curler or the substrate.

2. The blood pressure measurement device according to claim 1, wherein the plurality of protrusions are formed of a thermoplastic resin material and are thermally swaged.

3. The blood pressure measurement device according to claim 2, wherein the curler and the substrate are formed of a thermoplastic resin.

4. The blood pressure measurement device according to claim 3, wherein
the plurality of protrusions, the curler, and the substrate are formed of similar materials, and
each of the plurality of protrusions is thermally welded to the curler or the substrate.

5. The blood pressure measurement device according to claim 4, wherein the curler and the substrate are integrally molded, and include a hinge portion with which the curler and the substrate are connected.

6. The blood pressure measurement device according to claim 1, wherein
the bag-like structure is longer in one direction, and
the substrate is divided into a plurality of portions in a longitudinal direction.

7. The blood pressure measurement device according to claim 1, further comprising at least one additional bag-like structure, the bag-like structure and the at least one additional bag-like structure being a plurality of bag-like structures, wherein
the plurality of the bag-like structures are stacked,
the plurality of insertion holes are provided in the welded portion of the bag-like structure facing the curler,
the plurality of protrusions are provided on the substrate, and
the plurality of junction target holes are provided in the curler.

* * * * *